(12) United States Patent
Lee et al.

(10) Patent No.: US 11,532,385 B2
(45) Date of Patent: *Dec. 20, 2022

(54) SYSTEM AND METHOD FOR HEALTHCARE SECURITY AND INTEROPERABILITY

(71) Applicant: Janssen Pharmaceutica NV, Beerse (BE)

(72) Inventors: Jessica Lee, Edison, NJ (US); Jun Morimura, Tokyo (JP); Michael Moschetti, Montville, NJ (US); John Vig, Irvine, CA (US); Marvin Quesada, Princeton, NJ (US)

(73) Assignee: Janssen Pharmaceutica NV, Beerse (BE)

(*) Notice: Subject to any disclaimer, the term of this patent is extended or adjusted under 35 U.S.C. 154(b) by 168 days.

This patent is subject to a terminal disclaimer.

(21) Appl. No.: 17/149,707

(22) Filed: Jan. 14, 2021

(65) Prior Publication Data

US 2021/0151136 A1  May 20, 2021

Related U.S. Application Data

(63) Continuation-in-part of application No. 16/703,848, filed on Dec. 4, 2019, now Pat. No. 10,931,437, (Continued)

(51) Int. Cl.
*G16H 10/20* (2018.01)
*G16H 50/70* (2018.01)
(Continued)

(52) U.S. Cl.
CPC ............ *G16H 10/20* (2018.01); *G16H 10/60* (2018.01); *G16H 20/10* (2018.01); *G16H 50/70* (2018.01); *G16H 50/80* (2018.01)

(58) Field of Classification Search
CPC ..... H04L 9/0618; H04L 9/50; H04L 2209/42; H04L 2209/88; H04L 9/3239;
(Continued)

(56) References Cited

U.S. PATENT DOCUMENTS

2017/0091397 A1* 3/2017 Shah ..................... H04L 63/20
2018/0198624 A1* 7/2018 Bisti .................... H04L 9/3239

* cited by examiner

*Primary Examiner* — Huan V Doan
(74) *Attorney, Agent, or Firm* — McDermott Will & Emery

(57) ABSTRACT

Embodiments facilitate interoperability and secure patient selection for clinical trials and drug/device deployments. An entity may obtain a first set of health parameters and collective demographic information associated with one or more population segments and receive Electronic Health Record (EHR) sub-blocks with patient profile information and corresponding patient medical histories for patients. The entity may determine a subset of eligible candidate patients for a treatment based on information in the EHR sub-blocks and eligibility criteria for the treatment, which may be based the first set of health parameters, and/or the collective demographic information. The entity may transmit sub-blocks comprising eligible candidate patient profiles and medical information associated with the at least one treatment, and, in response to a received transaction block with a transaction confirmation, the entity may augment a multi-dimensional blockchain by linking: the transaction block, with a drug device information block and an EHR block.

20 Claims, 13 Drawing Sheets

Related U.S. Application Data which is a continuation of application No. 16/251,980, filed on Jan. 18, 2019, now Pat. No. 10,541,807.

(51) Int. Cl.
*G16H 20/10* (2018.01)
*G16H 10/60* (2018.01)
*G16H 50/80* (2018.01)

(58) Field of Classification Search
CPC ...... G16H 10/60; G16H 15/00; G06F 21/602; G06F 21/64; G06F 21/6245
See application file for complete search history.

SYSTEM AND METHOD FOR HEALTHCARE SECURITY AND INTEROPERABILITY

CROSS REFERENCE TO RELATED APPLICATIONS

This application is a continuation-in-part of U.S. patent application Ser. No. 16/703,848 entitled, "SYSTEM AND METHOD FOR HEALTHCARE SECURITY AND INTEROPERABILITY," filed Dec. 4, 2019, which is a continuation of U.S. patent application Ser. No. 16/251,980 entitled, "SYSTEM AND METHOD FOR HEALTHCARE SECURITY AND INTEROPERABILITY," filed Jan. 18, 2019 (now U.S. Pat. No. 10,541,807). The above-identified applications are hereby incorporated by reference herein in their entireties.

FIELD

The subject matter disclosed herein relates to healthcare system security and interoperability, and more specifically to supporting patient clinical trial selection and medical product deployment.

BACKGROUND

Healthcare information systems face compliance challenges that limit interoperability. For example, stored information may be subject to various privacy regulations such as Health Insurance Portability and Accountability Act (HIPAA). Privacy rules under HIPAA establish national standards to protect individual medical records and other personal health information when health care transactions are conducted electronically. These regulations may cover privacy (e.g. which entities have access to information), content (what information an authorized entity may access), security (how the information is protected from unauthorized access when stored and during electronic communication), information sharing (the types of information that entities may share), and integrity (the accuracy and authenticity of information). In addition, commercially valuable information may be protected under an organizational policy that may limit sharing of the information with third parties (e.g. as trade secrets, and/or for business or commercial reasons). Regulations such as the European Union (EU) General Data Protection Regulation (GDPR) and state regulations may also impact information collection, storage, sharing, and communication. These regulations have affected information sharing practices between healthcare marketplace participants and led to the creation of organizational "data silos," where information available to an entity is isolated, even when it could be useful systemically (e.g. to another non-competitive entity). Such compartmentalization of information has led to increased difficulty in selecting appropriate patients for participation in clinical trials and decreased efficiencies in conducting clinical trials. For example, patient pre-screening may involve manual screening by health care provider, manually contacting patients individually for approval, further screening by a clinical trial review board, patient selection, patient consent, etc. all prior to the actual clinical trial. These inefficiencies can have negative consequences when trials are conducted in the midst of a health emergency and/or approved medical products need to be deployed quickly and effectively. In addition, these data silos also increase systemic costs (e.g. by limiting information available to a patient or medical provider when considering the costs of treatment alternatives, treatment locations, etc.), and/or raise patient risk (e.g. from drug interactions, prescription abuse, etc.), and/or limit the efficacy of outcome based approaches to medical treatment or remediation (e.g. making it more difficult and expensive to determine when a desired outcome has been achieved or compare metrics in approaches that achieve similar outcomes). Systems and techniques to address one or more of the above issues that would help facilitate healthcare information security while promoting interoperability between marketplace participants are therefore desirable.

SUMMARY

In some embodiments, a processor-implemented method may comprise: obtaining a first set of health parameters and collective demographic information associated with one or more population segments; receiving one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients; determining, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information; transmitting, one or more encrypted first sub-blocks decryptable by one or more corresponding second entities, wherein each transmitted first sub-block comprises at least one candidate patient profile and medical information associated with the at least one treatment; and, augmenting, in response to a received transaction block with a transaction confirmation, a multi-dimensional blockchain, wherein the multi-dimensional blockchain is augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment.

In another aspect, a computing device for a first entity may comprise: a memory, a communications interface, and a processor coupled to the memory and the communications interface. In some embodiments, the processor may be configured to: obtain a first set of health parameters and collective demographic information associated with one or more population segments; receive one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients; determine, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information; transmit, one or more encrypted first sub-blocks decryptable by one or more corresponding second entities, wherein each transmitted first sub-block comprises at least one candidate patient profile and medical information associated with the at least one treatment; and augment, in response to a received transaction block with a transaction confirmation, a multi-dimensional blockchain, wherein the multi-dimensional blockchain is augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment.

In a further aspect, an apparatus may comprise: means obtaining a first set of health parameters and collective demographic information associated with one or more population segments; means for receiving one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients; means for determining, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information; means for transmitting, one or more encrypted first sub-blocks decryptable by one or more corresponding second entities, wherein each transmitted first sub-block comprises at least one candidate patient profile and medical information associated with the at least one treatment; and means for augmenting, in response to a received transaction block with a transaction confirmation, a multi-dimensional blockchain, wherein the multi-dimensional blockchain is augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment.

In some embodiments, a non-transitory computer-readable medium may comprise executable instructions to configure a processor to: obtain a first set of health parameters and collective demographic information associated with one or more population segments; receive one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients; determine, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information; transmit, one or more encrypted first sub-blocks decryptable by one or more corresponding second entities, wherein each transmitted first sub-block comprises at least one candidate patient profile and medical information associated with the at least one treatment; and augment, in response to a received transaction block with a transaction confirmation, a multi-dimensional blockchain, wherein the multi-dimensional blockchain is augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment.

The methods disclosed may be performed by one or more of mobile computing devices, computers, including servers, cloud-based systems, etc. using computer-readable media or computer-readable memory.

BRIEF DESCRIPTION OF THE DRAWINGS

Embodiments of the invention will be described, by way of example only, with reference to the drawings.

In the figures, like reference numbers and symbols in the various figures, which depict certain example embodiments indicate like elements. For example, sub-blocks with similar information are referred to with the same reference numbers. In addition, multiple instances of an element may be indicated by following a first number for the element with a letter or with a hyphen and a second number. For example, multiple instances of an element 280 may be indicated as 280-1, 280-2, etc. When referring to such an element using only the first number, any instance of the element is to be understood (e.g. element 280 in the previous example would refer to elements 280-1, 280-2 . . . and/or 280-N). Further, in the figures below, an asterisk symbol ("*") associated with a reference number indicates that the element (or some portion thereof) may be repeated (e.g. for each instance of the element). For example, a prescription may include several drug instances, and a dosage field may be repeated for each drug instance.

The figures below also show hierarchies of records, which may comprise fields and sub-fields. Records include any fields (and some or all of sub-blocks) that are part of the record. Similarly, a field includes any sub-fields. Sub-fields may include additional sub-fields. In addition to laws/regulations governing information sharing, the fields in the sub-blocks that are shared between entities may depend on one or more of: the informational interface between the entities, the transaction type, the context in which the data is being shared, and the state of the transaction at the time the sub-blocks are being exchanged.

DETAILED DESCRIPTION

Disclosed embodiments facilitate healthcare system security while promoting healthcare system integrity, interoperability, treatment selection, and cost transparency.

Figure 1:
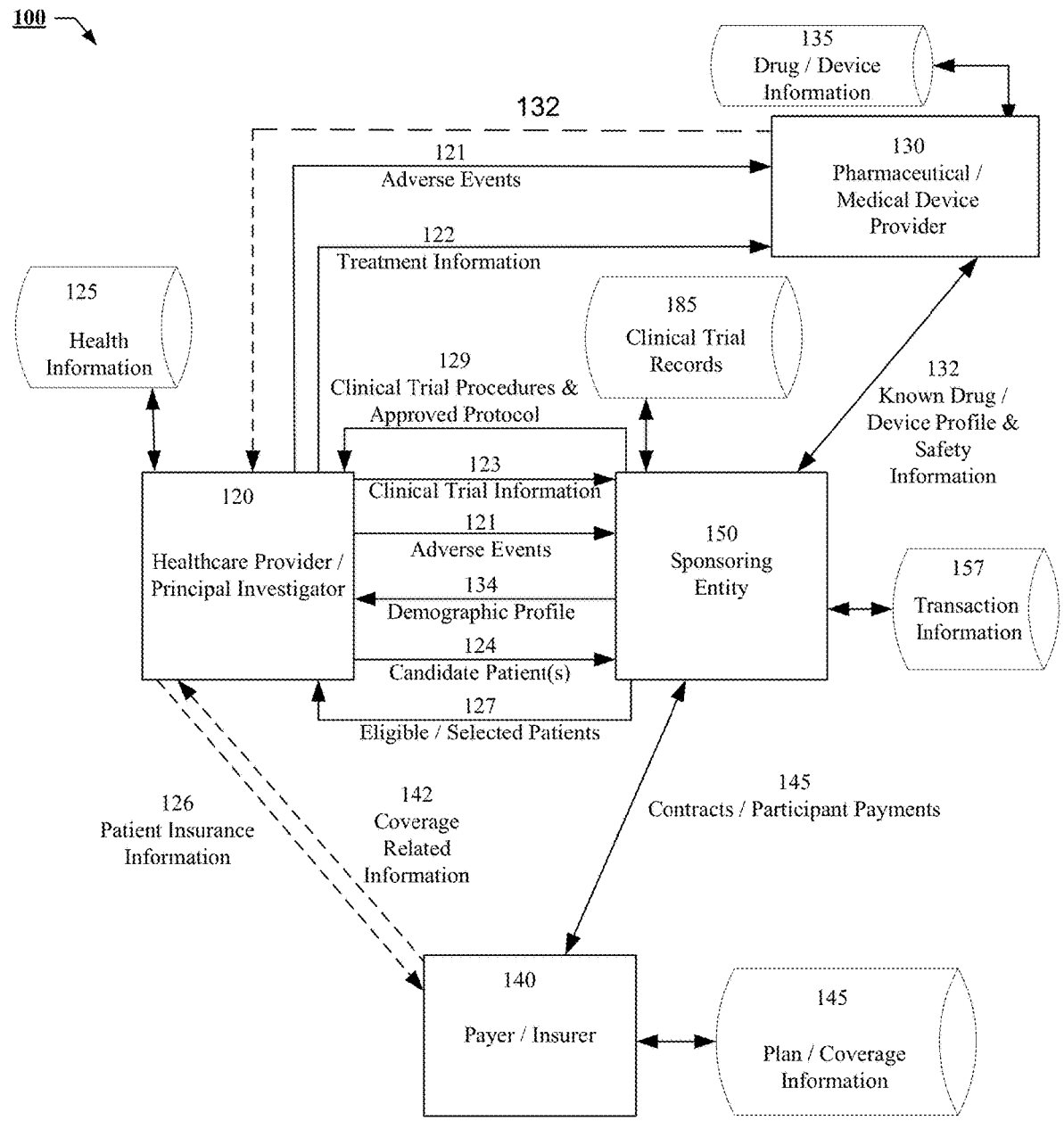
FIG. 1 shows a schematic block diagram illustrating interactions between some entities associated with a conventional healthcare information system.

FIG. 1 shows a schematic block diagram illustrating interactions between some entities associated with a conventional healthcare information system 100. FIG. 1 merely illustrates information flows associated with the entities shown and for transactions discussed. In general, various other entities (not shown in FIG. 1) and/or other types of transactions are envisaged.

Healthcare transactions may involve several entities, where each entity may have some transaction-relevant information, which may be used to complete the transaction. Thus, in conventional systems, some limited information (e.g. limited by regulation, contract, privacy considerations, confidentiality, and/or for competitive reasons) may be exchanged between the transacting entities in order to complete a transaction. The term "entity," as used herein, may refer to an individual (such as a patient or groups of patients) or an organization or that participates in a healthcare marketplace and/or to computing and information systems (e.g. hardware and/or software) associated with that individual/group/organization, which may participate in the healthcare marketplace on behalf of the individual/group/organization. For example, the computing systems associated with one entity may process and/or exchange information with computing systems associated with other entities. The exchange of information between entities may occur over secure communication networks and/or in a secure manner (e.g. using encryption) over the Internet and/or on an electronic platform (e.g. such as an information exchange and/or transaction exchange).

A Sponsoring Entity (SE) 150 may seek to conduct clinical research, which may include clinical trials and observational studies, to test scientific hypotheses and obtain scientific evidence. The clinical research may be conducted in accordance with applicable laws and regulations (which may vary by jurisdiction), as well as accepted and/or prevalent good clinical practices. The clinical research may be conducted for one or more drugs and/or devices. The term Sponsoring Entity (SE) 150 is used broadly to refer to any organization and/or division of an organization that may conduct clinical research. Thus, SE 150 may be an organization such as a university, research foundation, etc., and/or a division of an entity such as Pharmaceutical Provider and/or Medical Device Provider (PMDP) 130, and/or an entity hired by or in contract with an organization that conducts the clinical research on the organizations behalf, etc. As one example, SE 150 may be a division of a PMDP 130-$i$ and the clinical research may involve or include drugs/devices (e.g. to evaluate efficacy, performance, etc.) from competing PMDPs 130-$j$, $i \neq j$.

As another example, SE 150 (e.g. a division of PMDP 130-$k$) may submit an investigational new drug application (IND) to an appropriate authorizing agency such as the Food and Drug Administration (FDA) in the US. The IND application may include a protocol for the proposed clinical trial and any relevant past data to supports the proposed clinical trial. Upon approval of the IND application and protocol, SE 150 may commence the clinical trial process. In some instances, (prior to approval) the authorizing agency (e.g. FDA) may request protocol changes and SE 150 may go through protocol modification iterations (e.g. by revising the protocol appropriately and resubmitting) before it receives approval.

Upon receiving approval from the authorizing agency (e.g. the FDA), SE 150 may select one or more qualified Healthcare Providers (HCPs)/Principal Investigators (PIs) 120 (hereinafter referred to jointly as HCP 120 and/or HCP/PI 120) and provide them with proposed clinical trial procedures and approved protocol 129 to conduct the clinical research in accordance with the previously approved protocols and ensure proper monitoring of the investigations. In instances where the HCP 120 is also a Principal Investigator (PI) with responsibility for the clinical trial at a given clinical trial site, or the lead PI (e.g. leading the entire trial), HCP 120 may also referred to herein as PI 120 for clarity. HCPs/PIs 120 may request modifications to proposed clinical trial procedures 129 and the interaction between HCPs 120 and SI 150 may continue until agreement is reached on the clinical trial procedures to be used for the clinical trial.

The term SE 150 is also used herein to refer to any agency to which SE 150 may transfer some or all of its responsibilities (e.g. via contract). Typically, SE 150 may include, supervise, be monitored by, and/or interact with one or more other entities such as a Protocol Validator (PV), Clinical Trial Review Board (CTRB), Institutional Review Board (IRB), Data and Safety Monitoring Board (DSMB), etc., which may have specific responsibilities related to the clinical research. For example, the DSMB may evaluate and review accumulated trial's safety, conduct, progress, and efficacy. The IRB may review, modify, and monitor clinical research and procedures when human subjects are involved. The IRB may have the authority to approve, require modifications (e.g. to secure IRB approval), or disapprove research to ensure protection of the rights and welfare of human research subjects. SE 150 may provide and have access to some or all of the information obtained by the above entities associated with the clinical trial (subject to legal and procedural constraints).

SE 150 and PMDP 130 are shown as separate entities in FIG. 1 and described as such herein. Regardless of whether SE 150 and PMDP 130 form divisions of a single organization—data privacy, data de-identification, and various other procedural and legal considerations may limit data sharing between the divisions. Therefore, even when SE 150 and PMDP 130 are related, they may be viewed as separate entities based on data sharing, data privacy, and/or other considerations.

PMDP 130 may interact with SE 150 in relation to the proposed clinical trial/research study (e.g. involving human subjects) by supplying known Drug/Device Profile & Safety Information 132 (e.g. pharmacological information, dosage, drug interactions, safety updates, etc.) to SE 150, which may relay the information to HCPs 120. In some instances, HCP 120 may request and receive Drug/Device Profile & Safety Information 132 from one or more PMDPs 130 directly (e.g. when a plurality of drugs/devices are being clinically evaluated).

SE 150 may also store approved protocols 129 as part of Clinical Trial Record (CTR) database 185. In addition, SE 150 may also obtain clinical trial information 123 during the clinical trial, which may be used to determine efficacy, etc. SE 150 may also monitor the clinical trial (upon commencement) to ensure compliance with the clinical procedures and the approved protocol 129. An IRB associated with the trial may also receive periodic patient data about patient inclusion/exclusion and may offer input pertaining to the patient pool and/or determine feasibility based on actual patient recruitment relative to recruitment targets. Trial related information may also be stored by SE 150 in CTR database 185.

SE 150 may further select from candidate patients that match some demographic profile 134. For example, SE 150 may seek patients with demographic profile 134 that: (a) have one or more first medical conditions (e.g. hypertension), and/or (b) do not have one or more second medical conditions (e.g. do not have heart disease), and/or (c) are within some age group (e.g. 40-55), and/or (d) of a specified gender, (e) of some race or ethnicity, and/or (f) live in some designated areas (e.g. zip codes), and/or (g) are employed in certain professions, and/or (h) have certain lifestyles (e.g. non-smokers), etc. The demographic profile and categories above are merely examples and the profile may change considerably between trials (e.g. for clinical trials of different drugs/devices or different phases of a clinical trial for the same drug/device).

Accordingly, SE 150 may send demographic profile information 134 to another entity such as one or more Healthcare Providers (HCP) 120, which may help in the initial selection or prescreening of candidate patients 124 that appear to match demographic profile 134 for the clinical trial. HCPs 120 may refer to any healthcare provider or an institution with many healthcare providers. For example, a PI 120 may need to manually select and reach out to potential candidate patients to obtain initial approval prior to providing any candidate patient information 124 to PMDP 130. Upon receiving approval, information pertaining to candidate patients 124 from one or more PIs 120 may be sent to SE 150, which may determine some eligible patients 127 and provide information including an indication of eligible patients 127 to PIs 120. PIs 120 may then contact eligible patients 127 to obtain patient approval for participation in the clinical trial. Candidate patients who then agree to participate in the clinical trial, and are accepted by SE 150 may form selected patients 127.

Thus, information pertaining to each eligible patient 127 (who consents to participation in the clinical trial) may be sent by HCP 120 to SE 150. SE 150 may further screen the eligible patients 127 who consent to participation, and respond to HCP 120 with selected patients 127. The information exchanges between HCPs 120 and SE 150 may continue until SE 150 determines that the number of selected patients 127 is adequate for the clinical trial. The number of patients for a clinical trial may be determined during the exchange of proposed clinical trial procedure information 129 between HCP 120 and SE 150. In some instances, SE 150 may receive input from PIs 120 and/or statisticians to ensure that data obtained during the clinical trial is statistically relevant. Further, an IRB associated with the trial may also receive periodic patient data about patient inclusion/exclusion and may offer input pertaining to the patient pool and/or determine feasibility based on actual patient recruitment relative to recruitment targets.

Upon commencement of the clinical trial, SE 150 (and/or other entities/sub-entities) with specific responsibilities may monitor the clinical trial to ensure that the trial is compliant with the approved clinical trial procedures and protocol. During the trial, HCPs/PIs 120 may monitor patients, administer therapy, and record patient clinical trial information 123. For example, HCPs/PIs 120 (and/or another entity such as a DSMB associated with the clinical trial) may monitor clinical trial related procedures such as administration of the correct dosage, storage of drugs at the right temperature, etc., and may monitor and report patient related clinical trial information 129 (e.g. patient health parameters and other related information) to PMDP 130. Patient health information, clinical trial procedural information for the prescribed drug/device, etc. may be stored in health information (HI) database 125.

In some instances, SE 150 (e.g. an entity contracted with PMDP 130 and/or division of PMDP 130) may pay HCPs 120 and enrolled patients (drug trial participants) and may also reimburse the patients and HCPs 120 for costs incurred in relation to the clinical trial. In some situations (e.g. when a drug/device is being administered on a compassionate basis), then, for some selected patients 127, HCP 120 may also obtain and/or determine patient insurance and treatment information 123 based on HI database 125, which may be maintained by HCP 120. For example, an insurance provider may authorize treatment for some patients in certain situations.

HCP 120 may also send treatment information 123 to Pharmaceutical Provider and/or Medical Device Provider (PMDP) 130, which may respond with drug/device profile and safety information 132 for the drug/device being administered. The drug/device profile and safety information 132 may be stored in HI database 125. Clinical trial information 123, which may include treatment information that is sent to PMDP 130 may also be edited by HCP 120 to remove any patient personally identifiable information (PII).

Personally identifiable information (PII) is any data that could potentially be used to identify specific individuals. The term "non-PII" is used herein to qualify information that does not include PII. For example, a patient data record (with PII) may include a patient's name, full address, other identifiers (e.g. insurance identifier, driver's license number, social security number, and/or other identifying information) along with health related information. PII in the patient's data record may be removed to obtain a non-PII patient data record (without name, full address, and other identifying information). For example, the non-PII patient data record may include age, sex, medical history (e.g. medical conditions afflicting the patient, other medication being used by the patient, etc.), treatment(s), and optionally (e.g. when appropriate) a city, state, and/or zip code, and may include the full address of HCP 120 where the care was delivered.

PMDP 130 may send known Drug/Device profile and safety information 132 to HCP 120 based on information in Drug/Device Information Record (DIR) database 135 for the drug/device in the clinical trial. DIR database 135 may include drug/device profile and safety information 132. Further, drug/device profile and safety information 132 may include information about drug characteristics such as dosage, mode of administration, absorption, metabolism, duration of action, toxicity, and interactions with foods or other medications. Upon receiving drug/device profile and safety information 132, HCP may prescribe the one or more drugs and/or medical devices in the clinical trial at the appropriate dosage (e.g. as received from PMDP 130 and/or based on treatment specified as part of clinical trial procedure information 129). For example, in a clinical trial evaluation comparing a plurality of drugs, a dosages and other information for a drug-l may be specified in clinical trial procedure information 129, while dosages and other information for drugs-m, l≠m, may be obtained as drug/device profile and safety information 132 from one or more PMDPs 130.

As shown in FIG. 1, in some instances (e.g. when a drug/device is being administered on an emergency/compassionate basis), HCP 120 may, also securely send patient insurance and treatment (e.g. medical procedure related) information 126 to Payer/Insurer (hereinafter "Payer") 140. Payer 140 may be an insurer (e.g. when a drug/device is being administered on an emergency/compassionate basis). In other situations (e.g. when patients are being paid for participation in the clinical trial), Payer 140 may be a division of SE 150 or an agency contracted by SE 150 to effect payments to patients at specified intervals and/or upon completion of certain tasks/milestones. SE 150 and Payer 140 are shown as separate entities in FIG. 1 and described as such herein. As outlined earlier, regardless of whether SE 150, PMDP 130, and/or Payer 140 form divisions of a single organization—data privacy, data de-identification, and various other procedural and legal considerations may limit data sharing between the divisions. Therefore, even when SE 150, PMDP 130, and/or Payer 140 are related, they may be viewed as separate entities based on data sharing, data privacy, and/or other considerations.

Thus, patient insurance information 126 may be sent to Payer 140 in situations where a drug is being used for treatment (e.g. on compassionate or emergency use grounds) before the drug has been fully approved. Patient insurance information 126 may include patient ID and the proposed treatment (e.g. drugs and/or devices being prescribed). Patient insurance and treatment information 126 may include patient identification (ID) information, insurance plan information, group ID information, proposed treatment information (e.g. one or more of: medical procedure related information, drug related information, medical device related information, etc.). While insurance related and treatment information 126 may include some personally identifiable information (PII), the PII information shared may be limited. For example, regulations may indicate that patient insurance and treatment information 126 may not include patient family history and/or other patient information (which may be part of HI database 125) that is not relevant to coverage determination, and/or cost determination when being shared with Payer 140.

In a situation where approval is needed (e.g. when a drug/device is being administered on an emergency/compassionate basis), Payer 140 may compare the received patient coverage related information 126 with information in Plan/Coverage database 145 to determine coverage for the patient. Based on the coverage information, Payer 140 may update plan/coverage information database 145 and reply with a confirmation and/or additional/updated patient coverage related information 142 to HCP 120. Coverage related information may include coverage information related to the proposed treatment, and cost and payment related information such as patient co-pays, billing codes, etc. If Payer 140 approves the proposed clinical trial treatment, then HCP 120 may commence treatment and update information in HI database 125. On the other hand, if Payer 140 withholds approval and/or coverage for the proposed treatment is inadequate and/or does not meet the patient's cost criteria, the patient's enrollment in the clinical trial may be reviewed by SE 150, which may lead to further exchange of information between the entities (e.g. patient, HCP 120, SE 150, and/or the patient). For example, SE 150 may elect to: (a) pay for the costs (associated with the emergency/compassionate use) and/or to enroll the patient in the clinical trial (e.g. if enrollment is open and the patient meets enrollment criteria.

In other situations, such as where patients enrolled in a clinical trial are being paid, SE 150 and Payer 140 may share contract and participant payment information 145 in order to pay clinical participants and/or reimburse patients for costs. In addition, some PII information may be sent to Payer 140 (e.g. which may be a division of SE 150) and use the PII information for tax, financial, and/or accounting purposes. However, in the situation above (when patients enrolled in a clinical trial are being paid), Payer 140 may not receive medical treatment or other patient health related information for privacy, legal, and other reasons.

Thus, conventional healthcare information systems suffer from several drawbacks. While each entity obtains and maintains information that may be relevant for operating its business, very little of that information may be shared (e.g. due to legal, privacy, procedural, and/or business considerations) and when information is shared, it is often piecemeal, devoid of context, untimely, and may not be useful for decision making/planning purposes. For example, HCP 120 and/or patient may not have cost information related to a clinical trial treatment at the time of patient enrollment. As another example, when adverse drug effects 121 are reported by an entity (e.g. HCP 120 or a patient) to SE 150 and/or PMDP 130, validation of adverse drug effects may often be performed by another entity to determine if the adverse event can be attributed to the drug/device in clinical trial. Validation, which may involve additional entities, can introduce additional complexities that can further delay reporting and/or create additional silos thus affecting the timeliness and/or utility of the information (e.g. to SE 150 and/or PMDP 130).

In addition, because the information is compartmentalized and may be provided on an ad-hoc basis, aggregating the received information with information stored by the receiving entity may be cumbersome. Moreover, because each entity may index the information differently, it may be difficult for the receiving entity (or the sending entity) to tie received (or sent) information to an information record stored by the sending entity (or stored by the receiving entity). For example, if HCP 120 provides adverse drug effect information 121 to a PMDP 130 at some point in time, it may be difficult for HCP 120 and/or PMDP 130 to obtain additional patient or patient medical condition information that may be relevant to the adverse drug effect—even when that information may be legally shared.

Conventionally, while the use of blockchains to store health related information facilitates ensuring the integrity and authenticity of the stored information, conventional techniques do not address issues raised by data sharing or data movement between entities in an environment of increasing transactional and regulatory complexity—such as maintaining data privacy while decreasing information compartmentalization. Moreover, conventional techniques also do not ensure timely information availability (e.g. to one or more entities in a manner compliant with legal and regulatory obligations) to facilitate transaction finalization. Further, conventional techniques do not ensure that entities have a coherent and consistent view of completed transactions. The lack of a coherent and consistent view of completed transactions across entities can constrain interoperability, data utilization, and the quest for increased operational efficiencies. In addition, the constraints on interoperability often limit organizational ability to maintain a customer-centric focus because customer (e.g. patient) requests for information to aid or enhance decision-making (e.g. independently or in coordination with HCPs) may be difficult to accommodate.

Disclosed embodiments facilitate healthcare system security while promoting healthcare system integrity, interoperability, and facilitate healthcare cost transparency. Some disclosed techniques facilitate timely exchange (e.g. at the time of a transaction) of appropriate data (e.g. compliant with legal, privacy, and business guidelines) to appropriate entities (e.g. authorized entities associated with a transaction) to facilitate clinical trial patient enrollment and/or drug/device deployment, while facilitating a consistent and coherent view of the information across healthcare marketplace entities.

Interoperability is facilitated in part because multiple entities associated with a transaction may be able to tie appropriate relevant information shared during a transaction to the completed transaction using an agreed upon reference. Consistency and coherency are facilitated because locally recorded data (e.g. locally at an entity) may correspond to reference data (e.g. maintained on a shared platform) and each entity's view of the reference data (or portions of the reference data viewable by the entity) may be consistent with another authorized entity's view of the data (and/or with the other authorized entity's locally recorded data). In some embodiments, the reference data may be based on and/or take the form of a decentralized ledger. In some embodiments, the decentralized ledger may be accessible to authorized entities and each entity's view of the decentralized ledger may be compliant with legal, privacy, business, and/or contractual obligations. Further, efficiency is promoted because information relevant to decision-making is made available to entities early in the transaction cycle to facilitate early consideration of alternatives thereby decreasing the likelihood of and inefficiencies associated with transaction finalization and decreasing decision revisitation.

In some embodiments, a first entity (e.g., SE 150 and/or PMDP 130) may receive at least one encrypted first Electronic Health Record (EHR) sub-block (e.g. for a patient) that is decryptable by the first entity. The first EHR sub-block(s) may comprise patient medical coverage information for a patient and one or more first treatments (e.g. proposed drugs and/or devices, denoted by F_p, 1≤p≤P. The encrypted first EHR sub-block may be received (e.g. by SE 150 and/or PMDP 130) with a transaction ID for a current transaction and, in some instances, may not include PII information for the patient.

In some other instances, (e.g. when authorized and/or when SE 150 and/or PMDP 130 determines or uses patient eligibility to determine payment to patients and/or HCPs 120 for the clinical trial program), encrypted first EHR sub-block may be received (e.g. by SE 150 and/or PMDP 130) with a transaction ID for a current transaction and may further include PII information for the patient. In situations where patient PII information is received (e.g. by SE 150 and/or PMDP 130), then SE 150 and/or PMDP 130 may effect the payment and may use a locally maintained blockchain consistent with disclosed embodiments to maintain patient privacy on behalf of SE 150 and/or PMDP so that access to patient PII information is restricted to program administrators and/or authorized personnel. Authorization to provide PII information may be obtained prior to a transaction involving the sharing of patient data or may be pre-authorized by the patient (e.g. at the time of enrollment with HCP 120 or SE 150 or PMDP 130 or another entity). In some embodiments, the first EHR sub-block may further indicate that the patient has provided consent to use of information in the first EHR sub-block to determine clinical trial participation eligibility.

The first entity (e.g. SE 150 and/or PMDP 130) may determine patient participation eligibility for the patient in at least one clinical trial associated with at least one medical product (e.g. drug and/or device) based on (a) the received first EHR sub-block and (b) clinical trial records (CTRs) comprising one or more approved protocols, wherein each approved protocol is associated with a corresponding clinical trial for a corresponding medical product. For example, SE 150 and/or PMDP 130 may determine patient participation eligibility by comparing the patient's medical history, demographic information (e.g. age, gender, etc.) in the received first EHR sub-block and approved protocol information in clinical trial records (CTRs) for medical products that are undergoing clinical trials and enrolling new patients.

The first entity (e.g. SE 150 and/or PMDP 130) may transmit, based on the determination of patient participation eligibility (e.g. when the patient is determined to be eligible to participate in at least one clinical trial), at least one encrypted CTR sub-block comprising at least one approved protocol associated with the at least one clinical trial, and at least one encrypted Device/Drug Information Record (DIR) sub-block corresponding to the at least one medical product associated with the at least one clinical trial. For example, SE 150 and/or PMDP 130 may transmit: (a) CTR sub-blocks for one or more approved protocols, each associated with a corresponding clinical trial for which the patient is determined to be eligible; and (b) for each transmitted CTR sub-block, corresponding encrypted Device/Drug Information Record (DIR) sub-blocks for one or more corresponding medical products associated with the one or more clinical trials.

The first entity may receive, in response to the transmission, an encrypted second EHR sub-block decryptable by the first entity, wherein the second EHR sub-block comprises the patient profile information, a patient consent to participation in the at least one clinical trial, at least one second diagnosis code, and at least one second treatment code. For example, consent from the patient may be obtained after the HCP 120 (e.g. a trial coordinator or PI 120) advises the patient on the clinical trial. Patients interested in the clinical trial may provide consent. Accordingly, a patient (in consultation with HCP 120) may provide explicit consent to participate in one or more clinical trials. The second EHR block may also include one or more second diagnosis codes associated with conditions being treated, one or more treatment codes associated with drugs/devices being used for treatment. Some of the drugs/devices in the received EHR sub-block may be part of the at least one clinical trial.

Upon receipt of a transaction block with a transaction confirmation, the first entity may augment a multi-dimensional blockchain with a multi-dimensional block. The multi-dimensional block may be formed by linking: (i) the transaction block comprising the patient profile information, the patient consent, and the at least one clinical trial and the corresponding at least one approved protocol, (ii) a DIR block comprising medical information associated with the at least one medical product, and (iii) an EHR block comprising information associated with the second EHR sub-block. In some embodiments, the first entity may also augment a locally maintained blockchain with appropriate information pertaining to the clinical trial. The information in the block being added to the locally maintained blockchain by the first entity may correspond to information associated with the multi-dimensional block.

Some disclosed embodiments may also be used to deploy medical products effectively. For example, in situations, where there is an emergency (such as an epidemic, pandemic, or a localized emergent medical situation that affects a section of the population), it may be useful and effective to deploy medical products (e.g. vaccines/drugs, when availability is limited, and/or when production is still being ramped up prior to full availability) to sections of the population determined to be at higher risk (e.g. one or more of medical professionals, frontline workers, age groups, occupations, people with certain medical conditions, people living or working in a certain areas, affected people, etc.). For example, a government agency or a public health entity (hereinafter as "PHE") may determine the criteria for deployment of a therapy and disclosed embodiments may facilitate deployment based on the deployment criteria.

In some embodiments, the protocol for drug deployment in the emergent situation may be specified and/or mandated by a government/public health agency to address the emergent situation and deploy resources (e.g. vaccines/drugs) effectively to obtain favorable outcomes (e.g. control the spread of an outbreak). Accordingly, in some embodiments, a first set of health parameters and collective demographic information associated with one or more population segments may be obtained (e.g. at a first entity such as PMDP 130 and/or a pharmacy from a public health agency). For example, the first set of health parameters may be associated with at-risk or affected/infected populations.

Further, the first entity may receive one or more encrypted Electronic Health Record (EHR) sub-blocks decryptable by the first entity, wherein the one or more first EHR sub-blocks comprise: patient profile information for one or more patients, and corresponding patient medical histories for the one or more patients. For example, PMDP 130 may receive the one or more encrypted EHR sub-blocks from HCPs 120 that intend to prescribe certain products (e.g. vaccines or drugs to treat or protect against some infection) to patients to determine their eligibility to receive the drugs/devices.

In some embodiments, the first entity may determine, from the one or more patients, a subset of eligible candidate patients—eligible for at least one treatment—based on a comparison of information in the one or more EHR sub-blocks with corresponding eligibility criteria, wherein the corresponding eligibility criteria are based on one or more of: the first set of health parameters, or the collective demographic information. For example, the first entity may determine a set of eligible candidate patients (which may be a subset of the set of candidate patients) that are eligible to receive the drug/vaccine based on the demographic information or health parameters received from the public health agency.

The first entity may further transmit, one or more encrypted first sub-blocks decryptable by one or more corresponding second entities, wherein each transmitted first sub-block comprises at least one eligible candidate patient profile and corresponding medical information associated with the at least one treatment. For example, the first entity may transmit eligible candidate patient profiles for the subset of eligible candidate patients and medical information (e.g. dosage, drug interactions, contraindications etc.) associated with the at least one treatment (e.g. drug/vaccine) based on the corresponding eligible candidate profile (of the patient to receive the treatment).

In response to a received transaction block with a transaction confirmation, the first entity may augment a multi-dimensional blockchain with a multi-dimensional block. The multi-dimensional block may be formed by linking: (i) the transaction block comprising treatment deployment related information, (ii) a Drug-Device Information (DIR) block comprising medical information associated with the at least one treatment, and (iii) an EHR block comprising patient profile information, medical history, and prescription information for the at least one treatment. In some embodiments, the first entity may also augment a locally maintained blockchain with appropriate information pertaining to the treatment deployment. The information in the block being added to the locally maintained blockchain by the first entity may correspond to information associated with the multi-dimensional block.

The term sub-block indicates a portion of a data record or a block, which (when encrypted) may be decryptable by some specific entity or entities (but not by other entities). In the figures, sub-blocks are shown in dashed boxes. Information in sub-block(s) decrypted by a specific entity (or entities) may be incorporated into data records (or data blocks in blockchains) that are being maintained by that specific entity (or entities) when a transaction is finalized. For example, a transaction with a transaction ID U may involve entities A, B, C, and D, which may be owners of data records W, X, Y, and Z, respectively, in a multi-dimensional blockchain. In the example above, a data record W (owned by A) and related to transaction U may be encrypted and readable by the owning entity A (but not by other entities). However, the data record W may include (in addition to transaction ID U) a portion of the information in other data records (e.g. data records X, Y, and/or Z, which are not readable by entity A). For example, data from the one or more other data records (e.g. data records X, Y, and/or Z) that is present in W may have been received (e.g. by entity A) prior to transaction finalization as decryptable sub-blocks. Similarly, the other entities B through D may also include (in addition to transaction ID U) transaction related information present in a non-owned data records. For example, for entity B, information present in one or more of data records W, Y and/or Z, may have been received in the form of sub-blocks decryptable by entity B prior to transaction finalization. Thus, each entity A, B, C, and D may maintain distinct independent blockchains that include (for transaction U) data records W, X, Y, and Z, respectively, as blocks in their respective blockchains. The data records (or blocks) W, X, Y, and Z, associated with transaction U may also collectively form a multi-dimensional block in a multi-dimensional blockchain. Thus, a coherent and consistent view of the transaction is available to all marketplace entities that may be associated with a transaction while maintaining compliance with legal, privacy and/or other regulations/business considerations, and promoting data integrity.

The term "blockchain" as used herein, refers to a growable list of records or "information blocks" or "blocks," where the blocks are linked using cryptographic techniques. Each block includes a cryptographic hash of the previous block, a timestamp, and transaction data. A current block being added to the blockchain is also termed the head of the blockchain. A cryptographic hash function maps data of arbitrary size to a bit string of a fixed size, which is termed a "hash." Hash functions can be deterministic (the same input will produce the same output) and may be one-way functions that are infeasible to invert (i.e. determine the original data input from the hash value). The transaction data for a block may be represented as a Merkle tree root hash. The term "Merkle tree" or "hash tree" is used to refer to a tree, where every leaf node is labeled with a hash of the transaction data and each non-leaf node is labeled with the cryptographic hash of the labels associated with its child nodes. A block header for a block to be added to the blockchain may include a hash reference to the previous block header and a hash reference to the root of the Merkle tree that contains the transaction data. Blockchains promote data integrity because alterations to data in the blockchain results in inconsistencies in one or more of the hash references. The term record or data record is also used to indicate non-final data that is to be added to a blockchain. Once a data record has been validated and finalized the data record may be added to the blockchain and form a block in the blockchain.

The term "multi-dimensional blockchain" is used to refer to a sequence of multi-dimensional records (also referred to as multi-dimensional blocks), where each multi-dimensional record includes two or more data records. In some instances, each of the data records that may be viewed as forming a dimension of the multi-dimensional blockchain may also form blocks in a distinct blockchain associated with some entity. Thus, in some embodiments, a multi-dimensional block may comprise a data record in each dimension, where the data record corresponding to a dimension may form a block in a distinct conventional blockchain associated with a corresponding entity. For example, a multi-dimensional block may include an EHR data record as one dimension, a DIR data record as another dimension, and a Transaction data record as a third dimension. Further, in some instances, the EHR data record associated with a multi-dimensional block (in the multi-dimensional blockchain) may separately form a block in a distinct EHR blockchain (i.e. distinct from the multi-dimensional blockchain). Similarly, in some instances, the DIR data record and Transaction data record associated with a multi-dimensional block may each form a block in a distinct DIR blockchain (e.g. associated with PMDP 130), and a Transaction record blockchain (e.g. associated with Payer 140), respectively. Thus, in some instances, a data record in the context of the multi-dimensional blockchain may correspond to a block in a distinct conventional blockchain. In some instances, each data record (e.g. associated with a dimension) in the multi-dimensional block may correspond to, form part of, and/or or be derived from corresponding blocks in distinct conventional blockchains. The multi-dimensional block may include a cryptographic hash of a previous multi-dimensional block, a timestamp, and data. The data for the multi-dimensional block may include hashes of the individual data records that make up the multi-dimensional block. In some embodiments, a consensus mechanism between the entities may be used to confirm correctness of data in a proposed multi-dimensional block before that multi-dimensional block is committed and locked.

Thus, the multi-dimensional block may comprise two or more encrypted data records, where each encrypted data record may be associated with a distinct entity (e.g. in the healthcare marketplace). As outlined above, the data records in a multi-dimensional block may separately form blocks in distinct blockchains, where each of the blockchains may be associated with a distinct entity. Each encrypted data record may be decrypted by the corresponding associated entity (e.g. the data record owner). Further, an encrypted data record may include portions (termed "sub-blocks") with data that may have been decrypted by at least one other specific entity in addition to the encrypted data record owner. For example, the sub-block may have been decrypted by at least one other distinct entity (in addition to the data record owner) at the time the corresponding multi-dimensional block was formed. In some embodiments, at or prior to the time of multi-dimensional block formation, the sub-blocks may have been separately encrypted and made available to another entity along with information to decrypt the sub-blocks. Accordingly, a multi-dimensional block may facilitate availability of transaction data to a plurality of entities associated with a healthcare marketplace, while providing a coherent and consistent view of the data to authorized marketplace entities, complying with privacy and/or data sharing regulations, business guidelines, and/or contractual obligations, and promoting data integrity. Entities may also ensure data correlation (e.g. of a record associated with a dimension of a multi-dimensional block in the multi-dimensional blockchain) with a corresponding block in a locally maintained blockchain. In embodiments, when information is exchanged between two entities using sub-blocks, the information exchanged via the decryptable sub-blocks may be based on an informational interface between the two entities. In some embodiments, when exchanging information (e.g. at the time of multi-dimensional block formation), each entity may encrypt blocks associated with a local blockchain maintained by the entity while generating sub-blocks that are decryptable by the other entity. The informational interface may be based on a smart contract associated with the blockchain.

The term "smart contract" is used to refer program code or logic, which, in some instances, may be associated with a blockchain or a blockchain platform. The "smart contract" may encode rules or agreement between two or more entities in relation to data sharing, transactions, access, contract fulfillment, etc. The smart contract may be based on a contract between two or more entities and/or agreements related to the multi-dimensional blockchain platform. For example, "smart contract" program code associated with the multi-dimensional blockchain may process transaction requests and determine the validity of transactions based on program logic.

Figure 2:
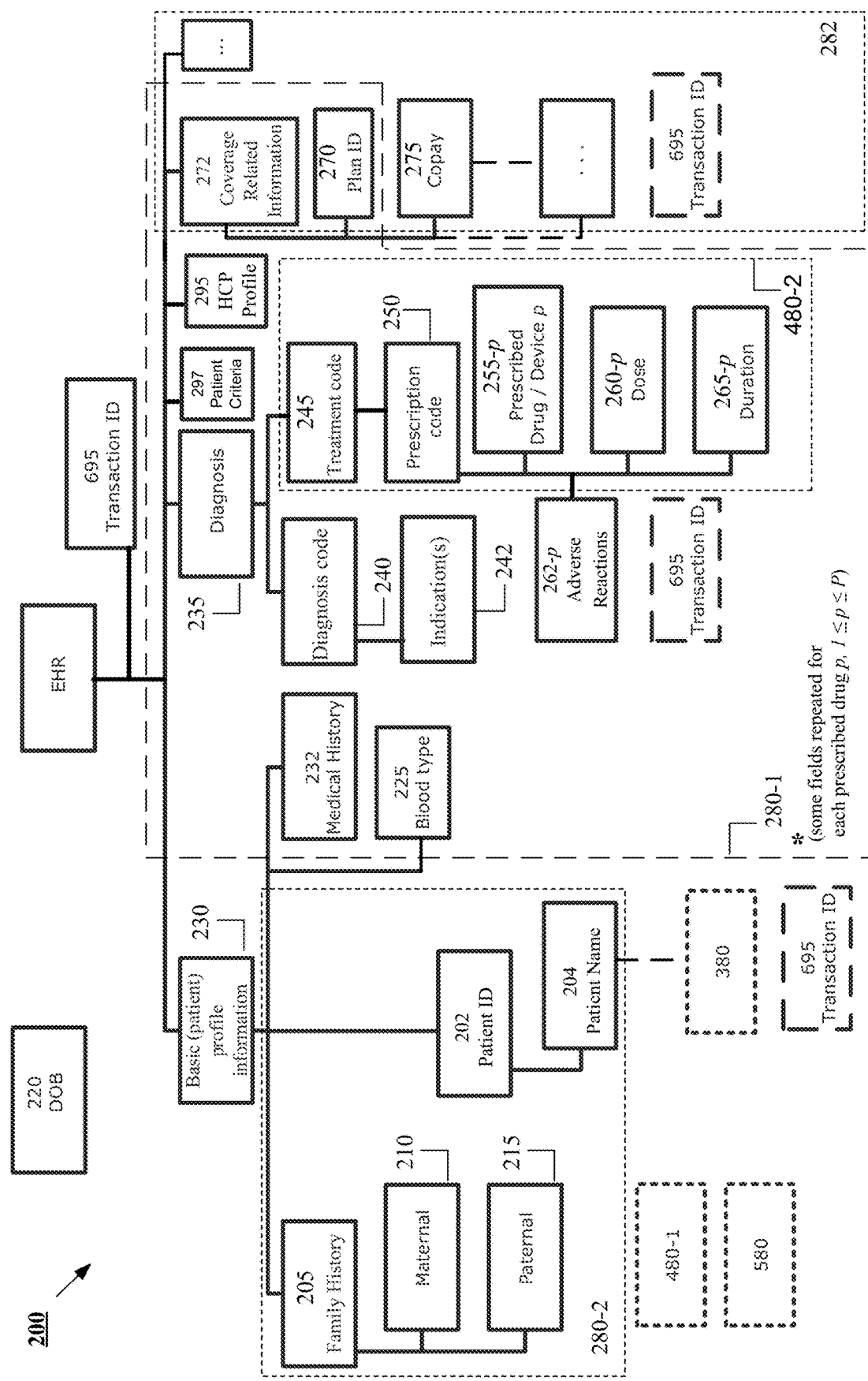
FIG. 2 shows an exemplary Electronic Health Record illustrating some exemplary data fields in a record.

FIG. 2 shows an Electronic Health Record (EHR) 200 illustrating some exemplary data fields in a record. In some embodiments, EHR 200 may include information about a patient and may be owned and maintained by HCP 120 (e.g. in HI database 125). In some embodiments, data fields in EHR 200 may be populated and/or updated by HCP 120 based, in part, on information received from a patient. EHR 200 may also include data received (e.g. as sub-blocks such as sub-blocks 380, 480, 580, etc.) from other entities such as PMDP130 and/or SE 150 and/or Payer 140. In some embodiments, EHR 200 may also include sub-blocks from other entities such as a Data and Safety Monitoring Board (DSMB) sub-block and a Food and Drug Administration (FDA) sub-block (not shown in FIG. 2). The DSMB sub-block, for example, may include information associated with a DSMB. DSMB may review clinical trial data on a periodic basis to ensure the safety of study subjects and validity and integrity of the data. The DSMB may review and evaluate accumulated clinical trial data for participant safety, clinical trial conduct and progress, and/or efficacy. The DSMB may also specify event triggers that would call for an unscheduled review, stopping procedures that are inconsistent with the approved protocol etc. Similarly, an FDA sub-block may include information for the FDA and/or another regulatory agency overseeing the trial and/or that approved the protocol for the trial. The fields shown in EHR 200 are merely exemplary, and EHR 200 may comprise various other additional fields based on laws, standards, HCP practice, and/or industry practice, etc. An EHR may comprise fields different from (fewer or greater than) those shown in relation to exemplary EHR 200. Sub-blocks 380, 480, and 580 are shown in dashed blocks to indicate that information received from the blocks may have been integrated into EHR 200.

EHR 200 may be associated with HCP Profile field 295, which may store information pertaining to HCP 120 (e.g. HCP identification, registration and/or licensing information, address, associated medical professionals, medical professional identification/registration information, etc.). In some embodiments, some or all of the information in HCP Profile 295 may be shared with other entities in connection with a transaction. For example, a portion of HCP Profile 295 may be sent to one or more entities such as PMDP 130, Payer 140, and/or SE 150 (e.g. as part of an encrypted sub-block 280, which may be decryptable by the designated receiving entity).

As another example, as shown in FIG. 2, EHR 200 may comprise basic profile information 230 about a patient, which may change relatively infrequently. Basic Profile information 230 may include Patient Name 204, Patient ID 202, Family History 205, Date of Birth (DOB) 220, Blood Type 225, etc. Family History 205 may include Maternal History 210 and Paternal History 215. Basic Profile Information 230 may also medical history 232, which may include information about other prior or current medical conditions associated with the patient.

In some embodiments, some of the basic profile information 230 may be considered as PII information (e.g. patient name 204, patient ID 202, etc.). In some instances, such as when a patient has consented to prescreening for participation in a clinical trial, and/or when a patient has consented to the use of patient related information for drug/device deployment, then, a portion of basic profile information (e.g. patient age, patient medial history 232, blood type 225, family history 205, patient zip code, etc.) may be shared with another entity as non-PII information (i.e. without any information that could uniquely identify the patient such as patient name 204, date of birth 220, patient ID 202, etc.) in a first sub-block 280 (e.g. limited to 280-1 without PII information). Once a patient has been selected as a candidate (e.g. for a clinical trial and/or for drug/device deployment), then, in some instances, additional patient consent may be obtained (if not already granted) as per applicable law/regulations, prior to sending out patient PII information in a subsequent sub-block 280 (e.g. including 280-2), which may be used to monitor the patient during the clinical trial and/or to schedule the patient to receive the prescribed drug/device during deployment.

EHR 200 may further comprise other data fields such as Diagnosis 235 (e.g. for a current ailment), Diagnosis Code 240, which may be a standardized code for the diagnosis (such as an International Classification of Diseases (ICD) code), Treatment Code 245, which may be a standardized code to describe the treatment (e.g. such as a Current Procedural Terminology (CPT) code), Prescription Code 250 for each prescription, which may serve to uniquely identify each prescription. Prescription code 250 is also referred to herein as prescription 250. ICDs include fields for diagnosis and medical procedures. For example, the FDA maintains a "dictionary" for unique drugs, where each drug is assigned a distinct number. Further, each dosage of the same drug may also be assigned a distinct identification number. Thus, drugs, dosages, and procedures may be uniquely identified from the ICD code.

In some embodiments, prescription code 250 (for a prescription) may include further include (e.g. for each drug/device being prescribed in the prescription) one or more subfields such as: a Prescribed Drug field 255-$p$, $1 \leq p \leq P$ (e.g. drug ID and/or a Classification Product Code (CPC) for medical devices), Dosage 260-$p$ (strength and frequency), and Duration 265-$p$ (length of time over which the drug is to be taken). In some instances, EHR 200 may also comprise other fields and/or sub-fields such as an indication of whether a prescription is a new prescription, or a refill. EHR 200 may also include adverse reactions field 262-$p$ such as Medical Device Report (MDR) adverse event codes, or other (e.g. ICD-10) codes to document adverse drug effects. In some embodiments, adverse reactions field 262-$p$ may be sent to SE 150 and/or PMDP 130 (e.g. when a patient is participating in a clinical trial) and/or to PMDP 130 (e.g. when prescribed as part of a drug/device deployment) as part of a sub-block 280. EHR 200 may also include Patient Criteria 297, which may specify one or more criteria for drug/device selection and/or cost metrics or cost criteria that may be provided by a patient. For example, Patient Criteria 297 may specify a preferred method of administration (e.g. topical, ingested, inhaled, etc.) when available, an area or location where prescribed drugs/devices are to be obtained, patient cost considerations, etc. For example, patient criteria 297 may be used during the pre-screening process for a clinical trial or to determine method of administration (e.g. ingested, topical, etc.) of a prescribed drug 255-$p$.

In some embodiments, EHR 200 for a patient may be stored as a blockchain, for example, by HCP 120. In some embodiments, information related to transactions between HCP 120 and the patient and/or another entity may form part of an EHR information block in the EHR blockchain. When an EHR block associated with a transaction is stored in a blockchain, the stored information may, in some instances, be associated with Transaction ID 695, which may serve to uniquely identify the transaction. In some embodiments, Transaction ID 695 may be common to entities associated with a transaction (e.g., all entities associated with a transaction may use the same transaction ID). In some embodiments, a transaction initiator and/or components of a permissioned blockchain platform may provide transaction information such as Transaction ID 695 to one or more entities associated with a transaction. Accordingly, sub-blocks sent or received by entities may be identified as being associated with a transaction and processed appropriately. In some embodiments, the format and content of Transaction ID 695 may be determined and/or agreed to in advance by entities associated with the transaction platform and/or provided by the transaction platform. Other transaction information related fields (not shown in FIG. 2) may include a transaction type, which may be used by an entity to determine and process information in transmitted and/or received sub-blocks and determine an appropriate response. For example, a transaction type may indicate that sub-block 480-1 is being provided (e.g. by SE 150) to specify parameters (e.g. prescribed drug/device, dose, duration, etc.) associated with a prescription for drug/device in a clinical trial. These parameters may then be used (e.g. by HCP 120) to populate and/or update corresponding parameters in EHR 200 (e.g. prescribed drug/device 255-$p$, dose 260-$p$, duration 265-$p$, etc.). The parameters above ((e.g. prescribed drug/device 255-$p$, dose 260-$p$, duration 265-$p$, etc.) may be provided, for example, by SE 150 (not shown in FIG. 2) upon selection (by SE 150) and approval by SE 150 and the patient for enrollment in a clinical trial.

In the description below, when an EHR is maintained as a blockchain (e.g. by HCP 120), then EHR information record 200 may also be referred to as EHR block 200. EHR block 200 may thus form a block in an EHR blockchain. When an EHR block 200 is to be added to an EHR blockchain, some of the data in EHR block 200 being added to the EHR blockchain may depend on other entities. For example, as outlined above, prescribed drug/device 255-$p$, dose 260-$p$, duration 265-$p$, may be provided by SE 150 in sub-block 480-1 upon selection and approval of a patient for a clinical trial. As another example, a treatment (e.g. specified in treatment code 245 for a diagnosis described by diagnosis code 240) may be subject to approval by Payer 140 (not shown in FIG. 2) and may be included as part of an EHR upon approval. As a further example, a drug warning label (not shown in FIG. 2), which may form part of EHR block 200 may use input from PMDP 130 (e.g. received in sub-block 380) to complete, validate, and/or update information in the warning label prior to EHR block 200 being added to the EHR blockchain.

In some embodiments, Patient Criteria 297, Diagnosis 235, Diagnosis Code 240, Treatment Code 245, Prescription Code 250 along with data fields Prescribed Drug/Device 255-$p$, Dosage 260-$p$, and Duration 265-$p$, $1 \leq p \leq P$, may form part of a sub-block 280. In some embodiments, upon approval (by SE 150 and the patient), sub-block 280 may further include PII information (280-2) such as one or more of: basic profile information 230, patient coverage related information 272 and/or plan ID 270, which may serve to identify an insurance plan (e.g. health insurance plan, pharmacy benefits plan, prescription coverage, etc.) subscribed to by the patient. In some embodiments, (depending on context, applicable laws, and/or patient authorization) sub-block 280 may (e.g. at an appropriate time during the transaction process) also include some or all of the information in sub-block 280 (280-1 and 280-2) and/or 282 described herein. Some or all of the information in sub-blocks 280 and/or 282 may be shared with one or more other entities (e.g. such as Payer 140 and/or SE 150) and may form part of other records/blocks associated with the transaction.

Prescription 250 may comprise one or more prescribed drugs/devices 255-$p$, $1 \leq p \leq P$, where P represents the number of drugs associated with a prescription 250. Thus, in some embodiments, sub-block 280 may comprise a record for each prescribed drug/device 255-$p$ in prescription 250. Sub-block 280 is merely an example that illustrates some information that may be shared with another specific entity. For example, sub-block 280, or a portion thereof (e.g. 280-1), may also be encrypted by HCP 120 and sent to PMDP 130 (e.g. without patient PII information in 280-2 to obtain safety and other information) and may be decryptable by PMDP 130.

In general, information in any appropriate field or combination of fields in a data record or block may be aggregated into a sub-block, which may be encrypted (e.g. by a first entity), so that the sub-block is decryptable by some other specific entity or entities (e.g. one or more second entities). The encrypted sub-block may be sent (e.g. by the first entity) to the other specified entity or entities (e.g. the one or more second entities), which may decrypt and act as appropriate (e.g. based on the transaction type) on the received information. The information that is used to form sub-blocks from a data record or a block in a locally maintained blockchain (e.g. an EHR blockchain) by a first entity and shared with another (second) entity may depend on regulations (e.g. healthcare and/or privacy), laws governing information sharing (e.g. which may determine information that can or cannot be shared between specific entities), business guidelines (e.g. which may govern sharing/protection of trade secret or sensitive information) and/or contractual obligations (e.g. between or related to the entities sharing information) and/or agreements (e.g. as part of a subscription to an electronic transaction platform).

As another example, information in sub-block 282 may include coverage related information 272, Plan ID 270, Co-payment information 275, etc. The coverage related information may be used during drug deployment when a treatment is paid for by an insurer such Payer 140 and/or when emergency/compassionate use of a drug/therapy may be approved by Payer 140 for a patient. In instances, where drug clinical trials are conducted and payments (e.g. to HCPs 120 and clinical trial participants) are made by PMDP 130, then, some sub-blocks (e.g. sub-block 282) may be omitted. As outlined previously, the number of sub-blocks may depend on the transaction type and the entities involved. When present, some information in sub-block 282 may have been obtained directly from patient, while other coverage related information may have been obtained from and/or confirmed by Payer 140 and decrypted by HCP 120 (e.g. based on one or more encrypted sub-blocks received from the appropriate entity and decrypted by HCP 120—not shown in FIG. 2) in connection with a transaction (e.g. to determine covered costs associated with compassionate use or administered during drug/device deployment) specified by Transaction ID 695. For example, a transaction type may indicate that sub-block 282 is being provided to obtain, confirm, or complete coverage related information 272 in connection with compassionate use or administered during drug/device deployment for prescribed drug/device 255-$p$.

Further, in some contexts, a portion of EHR information 200 (e.g. 280-1) such as some (e.g. non-PII) portion of Basic Profile information 230, DOB 220, Blood Type 225, and Medical History 232 may be encrypted by HCP 120 as a sub-block 280 and sent to SE 150 and/or PMDP 130 after prescreening a patient for clinical trial participation eligibility in connection with one or more drugs/devices. SE 150 and/or PMDP 130 may then decrypt sub-block 280 in connection with a transaction (e.g. to determine whether a patient meets criteria for enrollment in the clinical trial) specified by Transaction ID 695 and/or to determine patient/HCP payment when the patient has been selected for the clinical trial (after patient approval). As a further example, the portion of basic profile information 230 (e.g. 280-1) included in sub-block 280 may be non-PII (e.g. exclude name, identification number, etc.) related to a patient. Thus, medical information may be shared (e.g. to determine adverse reactions, medical device malfunctions, etc.) with another specific entity securely without compromising patient privacy. In another instance, where disclosure of PII information is permitted and authorized (e.g. by the patient), a sub-block may include PII information (e.g. 280-2 and/or 280-1) so that SE 150 and/or PMDP 130 can determine patient eligibility for payment assistance, or to report events including adverse reactions 262-$p$, other health parameters, and/or other outcomes during a clinical trial, or in relation to fulfilling a prescription (to establish patient identity) during drug/device deployment. For example, (depending on context, transaction type, applicable laws, and/or patient authorizations) some or all of the information present in 280-1, 280-2, and/or 284 may also be incorporated into sub-block 280.

As a further example, data in a sub-block 280 may be shared by an entity such as HCP 120 with another healthcare marketplace entity such as Payer 140 to complete a transaction. However, patient profile information (e.g. family history 205, maternal history 210, and/or paternal history 215) associated with Basic Profile Information 230 may be deemed private (e.g. based on patient instructions/privacy, legal, and/or business guidelines) and the first entity (e.g. HCP 120) may not share family history 205, or may limit the portion of Basic Profile Information 230 that is shared. In another instance, a non-PII portion of sub-block 280 may be shared initially by an entity such as HCP 120 with another healthcare marketplace entity such as SE 150 during pre-screening to determine patient eligibility for participation in a clinical trial and, at a subsequent time (e.g. upon selection by SE 150 of the patient for the clinical trial and after securing patient approval for participation in the clinical trial), sub-block 280 shared with SE 150 may include patient PII information.

Accordingly, in some embodiments, data used to form sub-blocks sent by an entity or received from another entity may depend both on the entities associated with a transaction (e.g. whether HCP 120 and Payer 140, or HCP 120 and SE 150), a current transaction state (e.g. whether a patient is being prescreened, or has been already selected for participation in a clinical trial and/or has indicated approval), and the context (e.g. type or nature of transaction, e.g. reporting adverse events, obtaining payment assistance, etc.) in which the data is being shared. In some embodiments, the informational interface between any two entities may depend on the transaction type, transaction state, and/or context. In some embodiments, one or more protocols (e.g. agreed to/prearranged by entities and/or set up by a permissioned blockchain platform and/or based on a standard) may specify transaction types and the information to be present in sub-blocks sent/received by an entity for each transaction type. In some embodiments, the data fields included in a sub-block shared between entities in connection with a transaction type may be indicated (e.g. by the protocol and/or agreed upon standard) as mandatory, conditional, optional, on request, etc. The indications (e.g. mandatory, conditional, optional, on request, etc.) may depend on the current transaction state.

Data in a sub-block (e.g. sub-block 280) may be separately encrypted and may be decryptable only by an authorized entity. In some embodiments, encryption of data that forms a sub-block (e.g. sub-block 280) may be based on any appropriate cryptographic method, including symmetric key encryption techniques (where the entities, such as HCP 120 and PMDP 130 share a secret key) such as Advanced Encryption Standard (AES) based techniques or variations thereof. Sub-block 280 may be encrypted (e.g. by HCP 120) prior to being shared with the other entity (e.g. Payer 140). The other entity (e.g. Payer 140) may be able to decrypt sub-block 280, for example, using the shared key.

Further, the data in EHR 200 may also be separately encrypted by HCP 120 using any secure encryption technique to form EHR block 200 prior to being added to a blockchain (e.g. maintained by HCP 120 and/or maintained by an electronic transaction platform). For example, the data in EHR block 200 may be separately encrypted using a private key (e.g. private to HCP 120), so that it is decryptable by and available to HCP 120 but unavailable to and/or not viewable any other entity.

Figure 3:
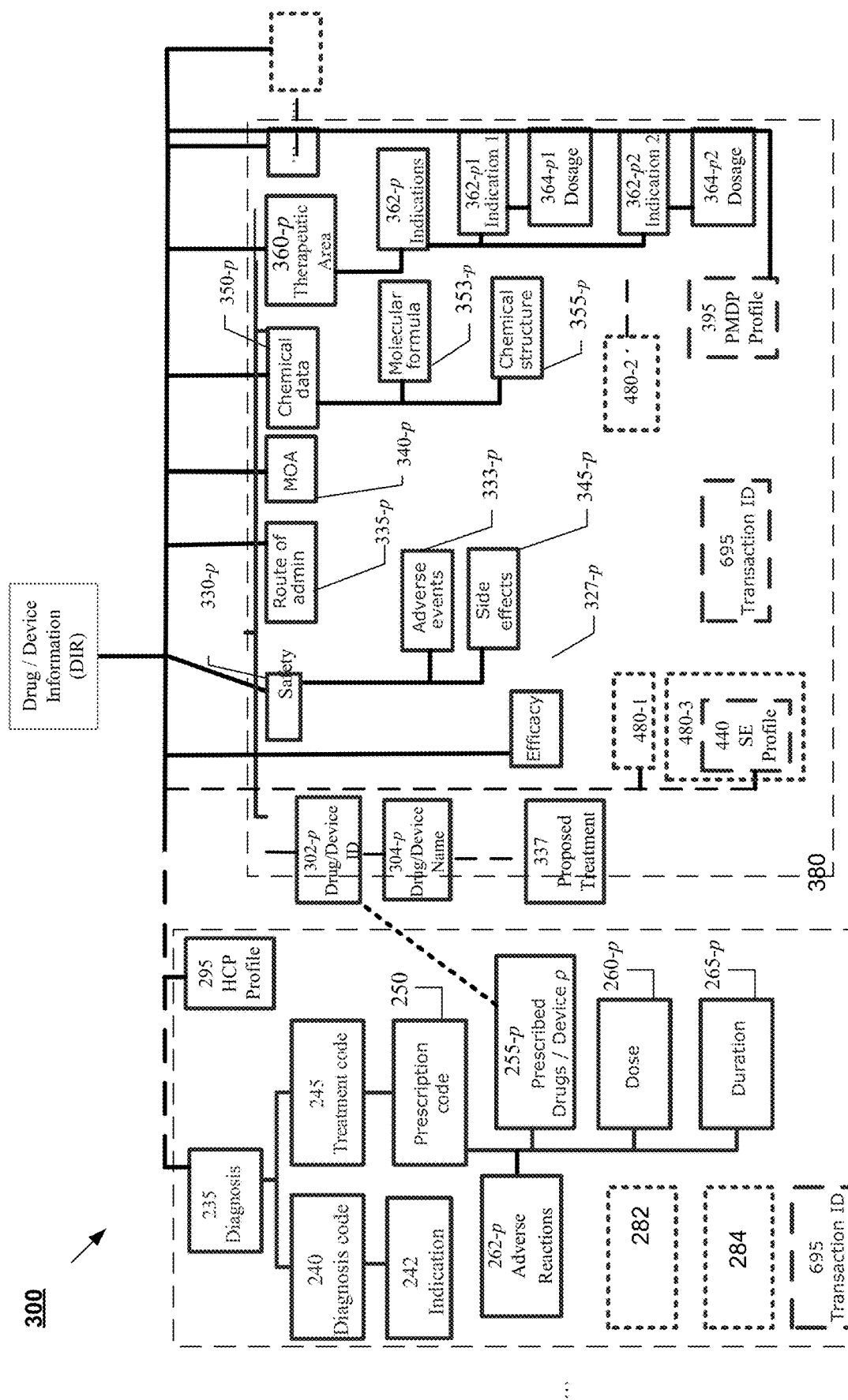
FIG. 3 shows a portion of an exemplary Drug/Device Information Record (DIR) for a drug/device, which may be stored in a DIR database.

FIG. 3 shows a portion of example Drug-Device Information Record (DIR) 300 for a drug, which may be stored in DIR database 135. In some embodiments, DIR 300 may include information about a treatment (e.g. drug and/or medical device) such as a drug, device, and/or procedure. The fields shown in DIR 300 are merely exemplary, and DIR 300 may comprise various other fields based on laws, standards, industry practice, etc. In addition, a DIR may comprise fields different from (fewer or greater than) those shown in relation to exemplary DIR 300. In some instances, such as when SE 150 is a division of PMDP 130, then the information in DIR record 300 may be maintained and/or provided by SE 150 during the clinical trial.

DIR 300 may be associated with PMDP Profile field 395, which may store information pertaining to PMDP 120 (e.g. PMDP identification, contact information, address, etc.). When SE 150 is a division of a PMDP 130 then the PMDP profile field 395 may correspond to information in SE Profile field 440. In some embodiments, some or all of the information in PMDP Profile 395 may be optionally shared with other entities in connection with a transaction. For example, a portion of PMDP Profile 395 may be sent to one or more entities such as Payer 140, and/or SE 150 (e.g. as part of an encrypted sub-block, such as sub-block 380, which may be decryptable by a designated receiving entity).

Referring to FIG. 3, PMDP 130 may use information in prescribed drug/device field 255-*p* (e.g. received as part of sub-block 280 from HCP 120) to determine (e.g. for each drug/device 255-*p* associated with prescription code 250) one or more of: an organ or biological system that the drug device treats, and/or a therapeutic area, which may be specified by Therapeutic Area field 360-*p* comprising repeating Indications sub-fields 362-*p*1, 362-*p*2 . . . ; repeating Dosage sub-fields 364-*p*1, 364-*p*2 . . . for a corresponding indication; mechanism of action and/or mode of action, which may be specified by MOA field 340-*p*; general chemical properties of a drug, which may be specified by Chemical Data field 350-*p*, which may further include sub-fields Molecular Formula field 353-*p* describing the drug's chemical components and Chemical Structure sub-field 355-*p*.

Referring to FIG. 3, DIR 300 may comprise various other data fields including Drug Name(s) 304-*p* for a drug/device ID 302-*p*, Efficacy 327-*p* (which may be a measure of therapeutic effect for a medical condition), Route of Administration 335-*p* (e.g. topical, oral, intravenous, etc.), Safety 330-*p* (e.g. drug interactions, toxicity, contraindications, etc.), which may include Side Effects sub-field 345 (e.g. secondary effects), and Adverse Events sub-field 333-*p* (e.g. adverse events reported for the drug, which may incorporate adverse reactions 262-*p* reported as part of sub-block 280 by HCP 120). DIR 300 may also include various other fields related to the drug/device.

In some embodiments, Drug/Device ID 302-*p*, Drug/Device Name 304-*p*, Safety 330-*p* (and sub-fields), and Efficacy 327-*p*, Drug/Device class 337-*p*, Therapeutic Area 360-*p*, Indications 362-*ph* (e.g. Indications 362-*p*1, Indications 362-*p*2, etc.), and corresponding Dosages 364-*ph* (e.g. Dosage 364-*p*1, Dosage 364-*p*2, etc.), may form part of sub-block 380. For example, information pertaining to Indications 362-*ph* (e.g. Indications 362-*p*1, Indications 362-*p*2, etc.), and corresponding Dosages 364-*ph* (e.g. Dosage 364-*p*1, Dosage 364-*p*2, etc.) for a drug/device undergoing clinical trial may be agreed upon by PMDP 130 and SE 150 as part of the protocol for the clinical trial.

Thus, the information sub-block 380 (and any other sub-block) may be pre-arranged between the entities, determined by protocol, and/or specified by the platform (e.g. based on laws, regulations, authorizations, and/or contractual obligations). Thus, information in sub-block 380 (and any other sub-block) may be more or less than that shown for an example sub-block (e.g. example sub-block 380) and may also depend transaction type, transaction context, and the interacting entities. Sub-block 380 may further optionally include Route of Administration 335-*p*, MOA 340-*p*, Chemical Data 350-*p*, and other related fields/sub-fields. In FIG. 3, fields associated with example sub-block 380 are shown enclosed within a dashed perimeter.

DIR sub-block 380 may be provided to another entity (e.g. HCP 120) by PMDP 130 in connection with a transaction (e.g. identified by Transaction ID 695). In some embodiments, information in sub-block 380 may be associated with a transaction (e.g. identified by Transaction ID 695 and a transaction type) and may be encrypted and transmitted by PMDP 120 to another entity (e.g. HCP 120) during the transaction and/or prior to transaction finalization.

In some embodiments, a DIR record 300 may be associated with a transaction (e.g. specified by transaction ID 695) and may be stored upon transaction finalization as a DIR block a DIR blockchain by an entity such as PMDP 130. In the description below, when DIR record 300 forms part of a DIR blockchain, then DIR information record 300 may also be referred to as DIR block 300. DIR block 300 may thus form a block in a DIR blockchain.

A transaction (e.g. specified by transaction ID 695) between two or more entities (e.g. patient, HCP 120, PMDP 130, Payer 140, and/or SE 150) may involve information (e.g. related to a drug/device) that is maintained (or owned) by another entity. For example, HCP 120 may request information from PMDP 130 pertaining to a drug/device undergoing clinical trial or being deployed. Prior to transaction confirmation, some of the data (e.g. maintained by PMDP 120 in a DIR information block 300), which is being integrated into records maintained by other entities (i.e. other the PMDP 130) may depend on input from, validation by, and/or confirmation by PMDP 130. Conversely, PMDP 130 may receive input from another entity (e.g. HCP 120) in the form of sub-blocks. Some or all of the received information may be incorporated into DIR record 300 and/or used to determine information in DIR record 300.

For example, HCP 120 may send sub-block 280 (e.g. with non-PII information) to PMDP 130. PMDP 130 may use information in sub-block 280 (e.g. a Prescribed Drug 255-*p*) to determine corresponding Drug/Device 302-*p*, drug/device class 337-*p* and obtain and provide the information in sub-block 380, which may be sent to HCP 120. HCP 120 may review the information in sub-block 380 (e.g. for drug interactions, adverse events 333-*p*, etc.) prior to administering the drug/device 255-*p* (which corresponds to drug/device 302-*p* in DIR 300) and finalizing a prescription.

In addition, PMDP 130 may store some of the information in a current (e.g. most recently received) sub-block 280 prior to transaction finalization as part of DIR record 300. For example, information pertaining to the diagnosis (e.g. Diagnosis code 240), dosage (e.g. Dose 260) adverse events (e.g. adverse reactions 262-*p* reported by HCP 120) etc. may be stored as part DIR record 300 and associated with corresponding Drug/Device IDs 302-*p* upon confirmation (e.g. from HCP 120) that the drug in Drug/Device ID field is being prescribed (e.g. as may be indicated by the value of Prescribed Drug field 255 in sub-block 280 at the time of transaction confirmation).

Accordingly, when information (e.g. related to the drug/device) pertinent to a transaction is requested, the owner (e.g. PMDP 130) may respond by sending the information (e.g. in sub-block 380) to the requesting entity (e.g. HCP 120), The information (e.g. in sub-block 380) may be encrypted (e.g. by PMDP 130) prior to sending and may be decryptable by the requesting entity (e.g. HCP 120) so that the information in sub-block 380 is private between the requesting (HCP 120) and sending (PNIDP 130) entities. In addition, information in the sub-blocks exchanged between entities may be restricted so that the information shared is compliant with existing regulations, privacy laws, contractual obligations, and/or authorizations received from a designated owner of the information (e.g. a patient).

Accordingly, in some embodiments, data in a sub-block sent to PMDP 130 may be separately encrypted by the corresponding sending entity (e.g. Payer-i 140-*i*) and may be decryptable by PMDP 130 and unavailable to unauthorized entities. In some embodiments, encryption of data in a sub-block (e.g. received by PMDP 130) may be based on any appropriate encryption technique including symmetric key cryptography. The encryption may be based, for example, on a secret key shared between the entities (e.g. Payer 140-*i*, identified in Payer 1 140-1 field and PMDP 130). The receiving entity (e.g. PMDP 130) may be able to decrypt the received sub-block, for example, based on the secret shared key.

Further, prior to being added to a blockchain, data in DIR block 300 may also be separately encrypted by a first entity (e.g. PMDP 130) using any secure encryption technique, so that it is decryptable by and available to the first entity (e.g. PMDP 130) but is unavailable and cannot be viewed by other entities (e.g. HCP 120 and/or Payer 140).

Figure 4:
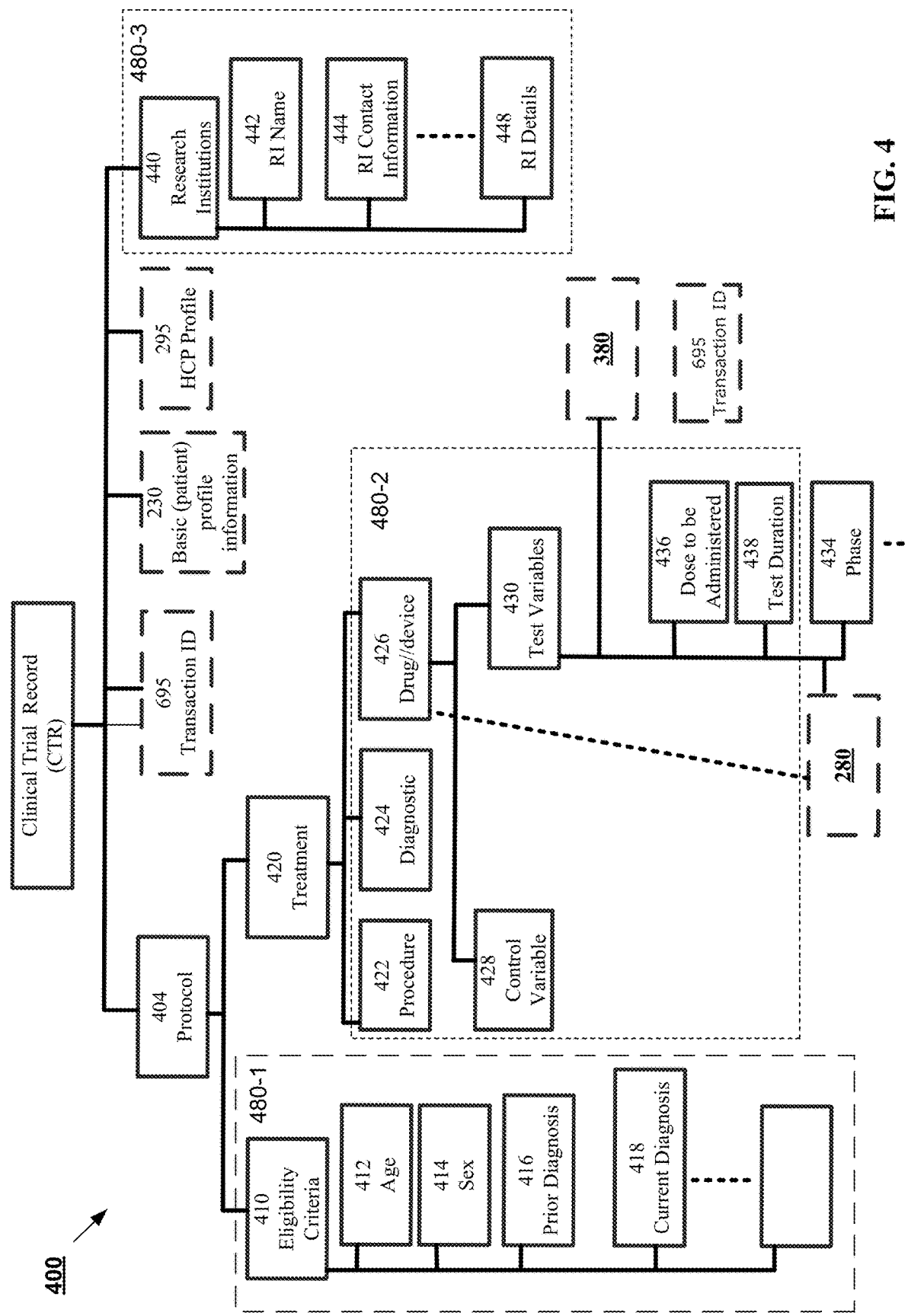
FIG. 4 shows a portion of exemplary Clinical Trial Record (CTR), which may be maintained by an entity conducting the clinical trial.

FIG. 4 shows a portion of exemplary Clinical Trial Record 400, which may be maintained by SE 150. The term SE is used to refer to any entity that serves to administer a clinical trial. SE 150 may have overall responsibility for communicating with PMDP 130, validating the clinical trial protocol, setting parameters to screen candidate patients, enrolling appropriate patients, monitoring the progress of the clinical trial, determining when to end the clinical trial, analyzing results, etc. Information pertaining to the clinical trial for a drug/device 255-*p* may be stored in CTR 400. CTR 400 may include information about protocol 404 for the drug/device 255-*p* in clinical trial.

CTR may include protocol field 404, which may include information pertaining to eligibility criteria 410 for patients. Eligibility criteria for patients may specify age 412 (which may be an age range), sex 414 (e.g. male), prior diagnosis 416 (e.g. any prior medical conditions), current diagnosis 418, etc. One or more of eligibility criteria 404 may be used to prescreen patients for a clinical trial. For example, information received in sub-block 280 (e.g. from HCP 120) may be compared with corresponding eligibility criteria 410 to select candidate patients for enrollment. In some embodiments, eligibility criteria 480-1 may be shared with HCP 120 to facilitate pre-screening by HCP 120 and/or as part of a decision to select (or decline) a candidate patient for a clinical trial.

Protocol 404 may also include treatment 420, which may specify a procedure 422 for the treatment, diagnostic 424 (to determine/confirm a medical condition), and drug(s)/devices 426. Clinical trials associated with a drug/device 426 may use a control variable 428 and test variables 430, which may specify dose to be administered 436, test duration 438, clinical trial phase (e.g. Phase 1, Phase 2, etc.), and may also include a treatment duration and other parameters. Some of all of the information above (e.g. in 480-2) may form part of a sub-block 480, which may be shared with HCP 120 upon selection of a patient for a clinical trial.

For example, HCP 120 may use some or all of the above information (e.g. 480-2) in sub-block 480 to advise the patient and/or to obtain coverage information from Payer 140 to determine costs associated with patient participation in the clinical trial (e.g. when administered on an experimental or compassionate basis) or to authorize payment to patients (e.g. when patients are being paid for participation). As an example, SE 150 may recommend drug device 426 (undergoing clinical trial) to HCP 120, which may revise a prior prescription 250 to include drug/device 462 (e.g. as drug/device 255-q), and then send sub-block 280 to (a) PMDP 130 to obtain information related to drug/device 462 (255-q) in sub-block 380 to advise patient, and (b) Payer 140 to obtain coverage related information.

In some embodiments, SE 150 may also send sub-block 480 with information 480-1 and/or 480-2 to PMDP 130 to determine and agree on protocol 404. PMDP 130 may respond with some or all of the information in sub-block 380. The exchange of information between SE 150 and PMDP 130 may occur prior to the start of the clinical trial and/or if one or more parameters need to be modified during the trial.

Sub-blocks 480 sent by SE 150 and/or received by SE 150 from another entity may include transaction ID 695, which may be used to identify a transaction associated with the sub-blocks. In addition, if an eligible candidate patient is determined (following prescreening) for potential enrollment in a clinical trial, then HCP 120 may (e.g. after obtaining patient approval in compliance with any laws/regulations etc.) send patient profile 230 along with PII information and drug/device 255-q to SE 150 in sub-block 280. In some embodiments, CTR 400 may also include HCP Profile 295 with information about HCP 120, which may be sent to SE 150 as part of sub-block 280.

In some embodiments, CTR 400 may also include information pertaining to SEs 150 such as research institutions (RI) 440 including RI name 442, RI contact information 444, RI details 448, and other information such as the principal investigator, etc. In some instances, a PI may be associated with multiple physical locations that roll up to a single research institution. For example a doctor can have rights with university hospitals, which may have many locations even within one city.

In some embodiments, the RI information 440 above pertaining to the research institution (e.g. as in 480-3) may form part of CTR sub-block 480. Further, in some instances, CTR sub-block 480 may include some combination of the information 480-1 and/or 480-2 and/or 480-3. Information in sub-block 480 (e.g. 480-3) may facilitate identification of RI 440 associated with the clinical trial.

Figure 5:
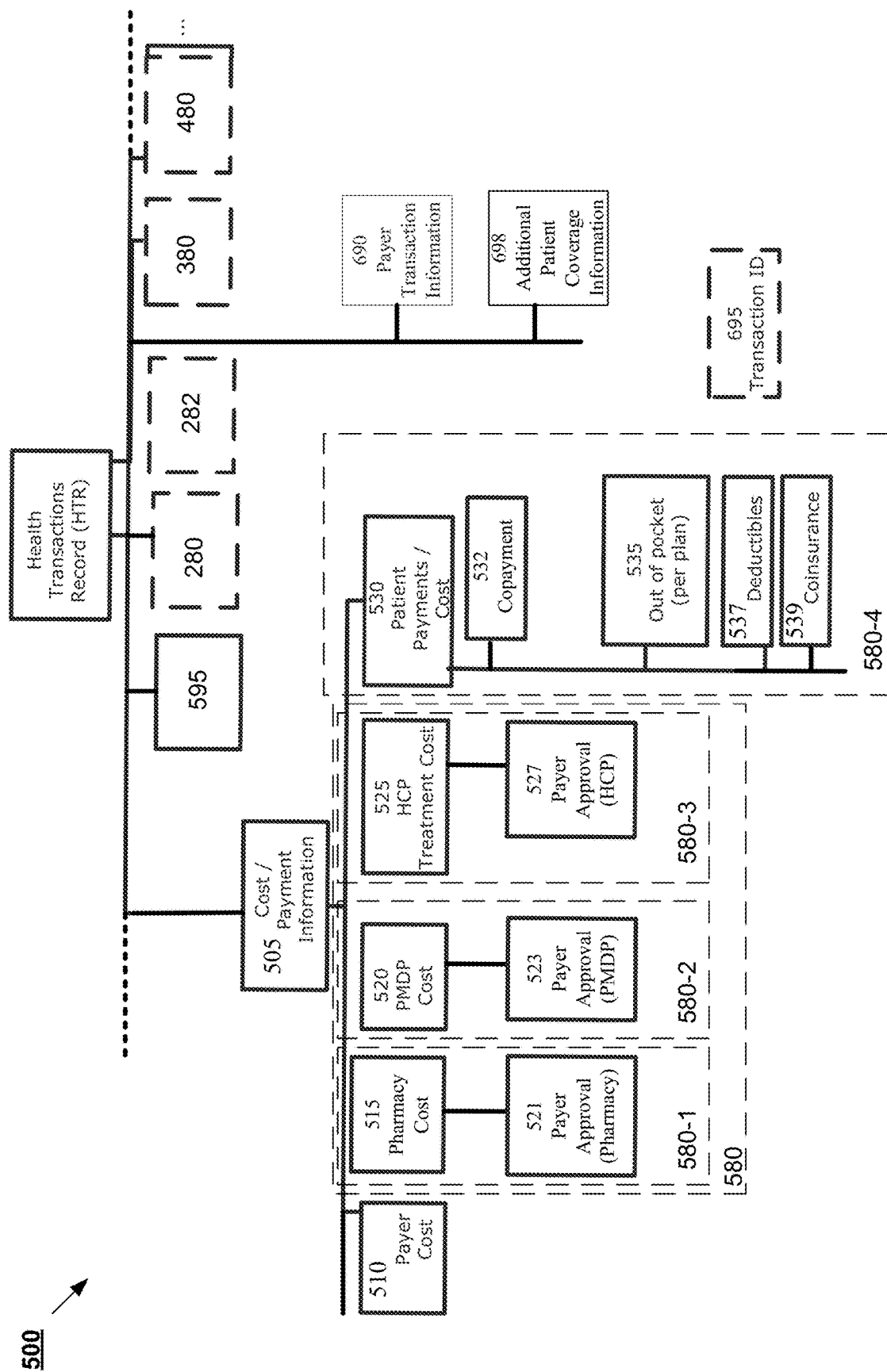
FIG. 5 shows an example Health Transaction Record

FIG. 5 shows an exemplary Health Transaction record (HTR) 500. As shown in FIG. 5, HTR 500 may include treatment and payment and/or cost related information for a transaction associated with a patient. The fields shown in HTR 500 are merely exemplary, and HTR 500 may comprise various other fields based on laws, standards, industry practice, etc. In addition, an HTR may comprise fields different from (fewer or greater than) those shown in relation to exemplary HTR 500. In some embodiments, HTR 500 may be owned and maintained by entity such as Payer 140 (e.g. SE 150 or a health insurer) and may and form part of Transaction Information database 157, which may be responsible for transaction approval and/or payments to one or more entities associated with a transaction.

HTR 500 may comprise various data fields including information about entities associated with and/or authorized to transact with Payer 140 including Patient profile 195, HCP profile 295, PMDP profile 395, SE profile 495, etc. The stored profiles may include information to effectuate transactions between the entities (e.g. payments, rebates, validations of coverage, authorizations for treatments/prescriptions, etc.) HTR 500 may also include HTR profile 595, which may include Payer name, Payer contact information, etc. and be used to identify and/or communicate with Payer 140.

In situations, where Payer 140 covers costs for experimental/compassionate use of a drug/device, HTR 500 may include Cost information 505, which may include Payer's view of costs associated with the transaction. For example, Cost information 505 may include Payer cost 510, which may record the net cost to Payer 140 for the transaction. Payer cost 510 may be a function of one or more of: Pharmacy Cost 515 (e.g. price charged by Pharmacy 160 to Payer 140), PMDP Cost 520 (e.g. negotiated price between Payer 140 and PMDP 120), HCP treatment cost 525 (e.g. cost for treatment provided by HCP 120 related to the diagnosis), and Patient cost 530 (e.g. patient out of pocket costs 535 as seen by Payer 140 under the plan, which may include patient copayment 532 for the treatment and prescription, deductibles 537, and coinsurance 539). Some of the information associated with Cost information 605 may be available to Payer 140 (e.g. based on contracts etc.), while some cost information 605 may be provided by other entities (e.g. via encrypted sub-blocks decryptable by Payer 140) prior to transaction finalization.

In the situation above (where Payer 140 covers costs for experimental/compassionate use of a drug/device), HCP 120 may send encrypted sub-block 280 with coverage related information 272, Plan ID 270 and/or HCP profile 295 (e.g. as in 280-1 and/or 282 in FIG. 2) to Payer 140. Payer 140 may decrypt the information in sub-block 280 (including 280-1 and/or 282) and validate patient coverage using additional patient coverage information 698. Validation of patient coverage may be provided to HCP 120 by sending to HCP 120 an encrypted HTR sub-block 580 (e.g. with information in 580-3 and 580-4), which is decryptable by HCP 120, with the validation information. In some instances, HCP treatment Cost 525 may be based on contractual agreements between Payer 140 and HCP 120, while in other instances, HCP Treatment Cost 525 may be sent to Payer 140 by HCP 120 providing the treatment in encrypted sub-block 280. As a further example, encrypted sub-block 280 (which, in some instances, may include information in 282) may be sent by HCP 120 (e.g. once a prescription for drug undergoing clinical trial has been determined) to Payer 140 for validation and transaction approval. In some embodiments, encrypted sub-block 280 may be decrypted by Payer 140 and Payer 140 may approve the transaction by sending one or more confirmation messages (e.g. to HCP 120) in the form of HTR sub-block 580 with payer approval (HCP) 527. Similarly, in response to a query from PMDP 130 (e.g. in relation to payment assistance to a patient participating in a clinical trial) an encrypted HTR sub-block 580 (e.g. with information PMDP Cost 520 and payer approval (PMDP) 523 in 580-2 and relevant information in 580-4), which is decryptable by PMDP 130, may be sent by Payer 140 to PMDP 130. As another example, in response to a query from a pharmacy (e.g. in relation to a prescription 250 associated with a patient participating in a clinical trial) an encrypted HTR sub-block 580 (e.g. with pharmacy cost 515 and payer approval (pharmacy) 521 in 580-2 and relevant information in 580-4), which is decryptable by the pharmacy, may be sent by Payer 140 to the pharmacy.

In situations, where SE 150 pays participants in the clinical trial, then, Cost/Payment information 505 may reflect payments made by SE 150 to entities associated with the transaction.

In some embodiments, upon transaction finalization, HTR 500 may be stored as part of a local blockchain maintained by and accessible to Payer 140. HTR 500, in encrypted form (and decryptable by Payer 140) may also form part of a multi-dimensional block in a multi-dimensional block. Information not in the HTR block 500 of the multi-dimensional blockchain may be encrypted by other entities and may not be decryptable by Payer 140. Conversely, HTR block 500 in the multi-dimensional block may not be decryptable by other entities associated with Payer 140 and/or the platform. Thus, while each entity has a consistent view of the transaction, which is recorded as a multi-dimensional block in a multi-dimensional blockchain, an entity cannot view information in blocks (stored as part of a multi-dimensional block) that are owned by other entities. Accordingly, information in a block (stored as part of a multi-dimensional block) owned a first entity is securely shielded from view by other second entities.

Figure 6:
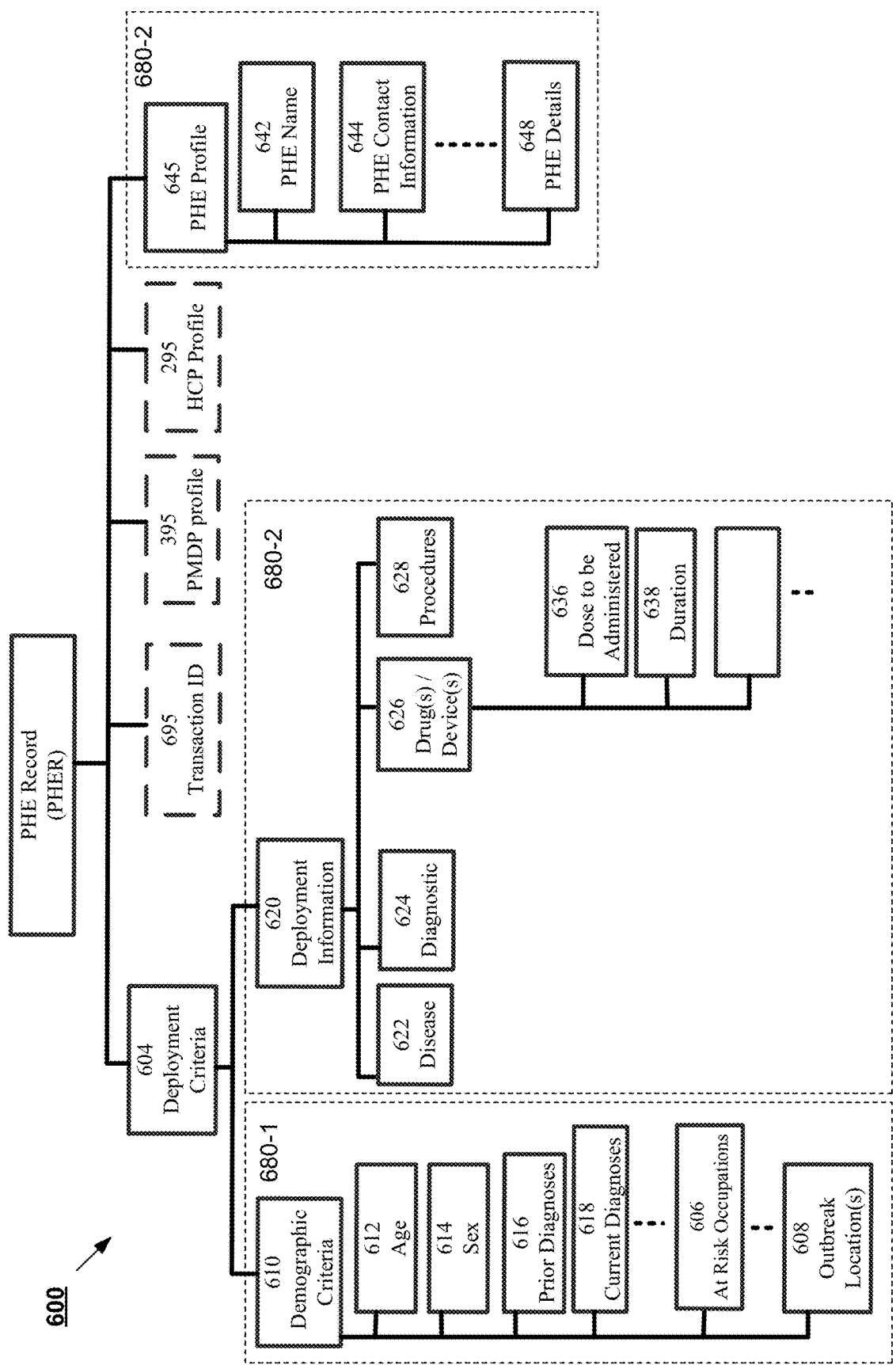
FIG. 6 shows a portion of exemplary Public Health Entity Record (PHER) 600, which may be maintained by a public health entity.
Figure 8:
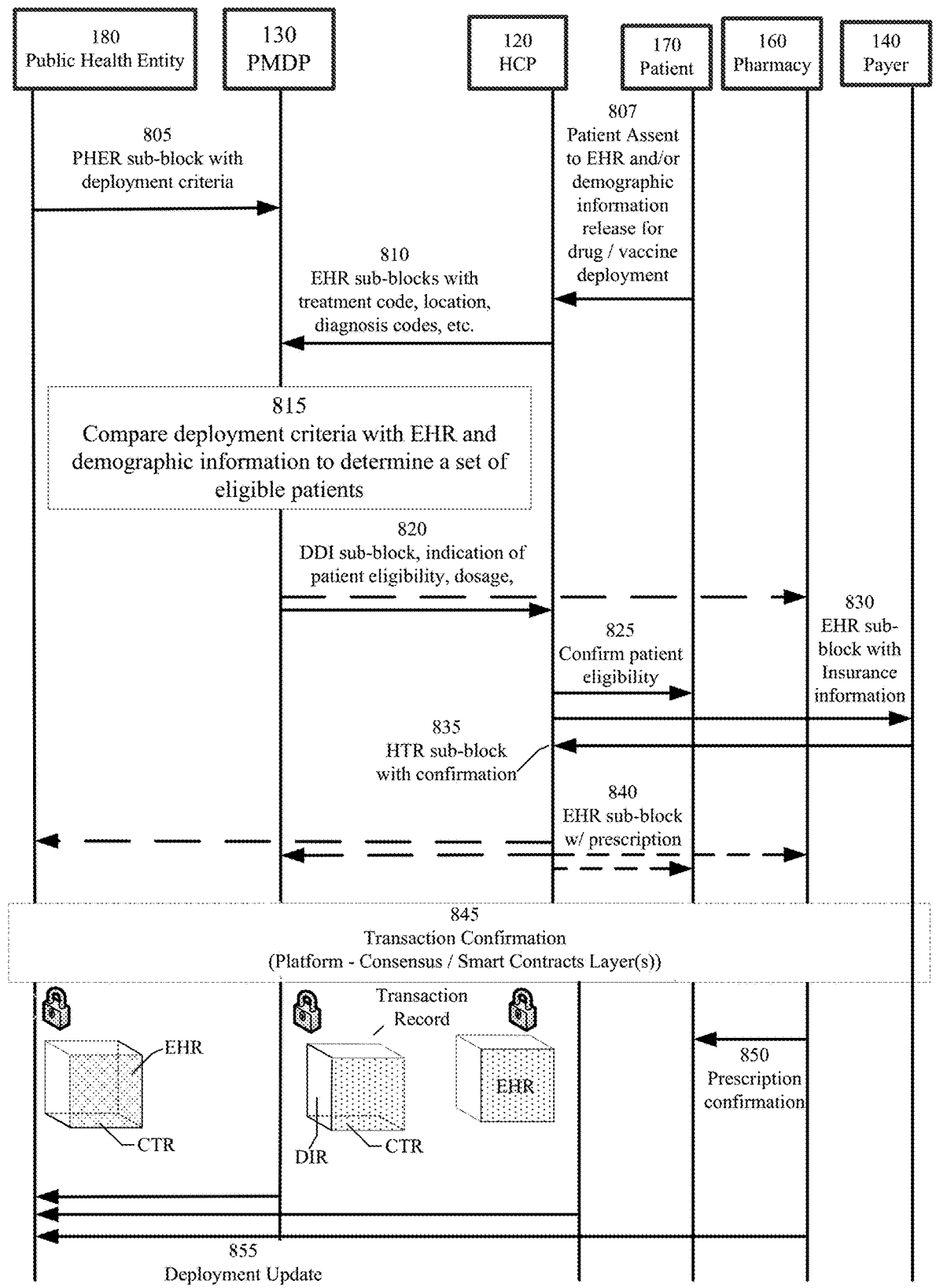
FIG. 8 shows a flow diagram illustrating an example process flow to facilitate secure drug/device deployment and promote interoperability between a plurality of entities.

FIG. 6 shows a portion of exemplary Public Health Entity Record (PHER) 600, which may be maintained by a PHE (such as PHE 180 in FIG. 8). The term PHE is used to refer to any entity that is tasked with acting to protect and/or advance public health interests. PHEs may operate at city, county, state, national, or international level and include government and regulatory organizations. PHEs may have overall responsibility for implementing public health measures including drug and/or device deployment following a public health emergency. In some embodiments, PHE 180 may maintain PHE record 600 based on information reported by testing and monitoring stations, HCPs 120, etc. In some embodiments, portions of PHER 600 such as demographic criteria 610 (e.g. including risk factors such as age, gender, occupations, health conditions, etc.) associated with one or more population segments (e.g. populations at heightened risk in relation to a health emergency) may be published, available and accessible publicly (e.g. via the Internet) and/or to authorized entities (e.g. HCPs 120, PMDPs 130, etc.).

In many public health emergencies, such as the Covid-19 pandemic, clinical trial of vaccines, drugs etc. often occur in close proximity to the deployment or rollout (once the vaccines, drugs, etc. have been approved). Deployment of the drugs, vaccines, devices (e.g. ventilators, etc.) are often phased because: (a) availability may be limited initially (e.g. as production is ramped up), or (b) some population segments may be prioritized to receive the drugs and/or devices (e.g. medical personnel, first responders, essential workers, populations deemed to be vulnerable because of demographics, or populations that may be at heightened risk such as those living in areas with a larger outbreaks, etc.). In the situations above, a streamlined process to facilitate rapid transition from clinical trial approval to prioritized and/or targeted drug deployment can improve health outcomes, help control and prevent disease spreading, ensure availability in affected areas/populations, decrease drug/device shortages in critical areas, and quicken a return to normalcy by shortening the overall length of the outbreak. Some disclosed embodiments, which enhance interoperability between healthcare entities, facilitate prioritized drug and/or device deployment. In some embodiments, PHER 600 may be used to facilitate prioritized and/or targeted drug and/or device deployment. In general, a PHER may comprise fields different from (fewer or greater than) those shown in relation to example PHER 600. In some embodiments, data fields in PHER 600 may be populated and/or updated based on information received from HCP 120, testing centers, and/or other entities/sources.

PHER 600 may include deployment criteria 604, which may include collective demographic criteria 610 such as age (or age range), 612, sex 614, etc. and health parameters such as prior diagnoses 616 (e.g. prior patient medical conditions), current diagnoses 618 (e.g. existing patient medical conditions), etc. which may identify elevated risk factors in relation to disease 628. Demographic criteria 610 may also include several other fields such as ethnicity, travel history, etc. (not shown in FIG. 6). Demographic criteria 610 may also include at-risk occupations 606 (e.g. occupations at higher risk for disease contraction), outbreak locations (e.g. zip codes or localities experiencing outbreaks, or increasing rates of infection, etc.), which may identify population segments at risk. Thus, PHER 600 may include collective demographic information (e.g. in demographic criteria 610) with risk factors and/or health parameters identifying at-risk populations.

In some embodiments, each risk factor may be associated with a risk weight, which may reflect the degree of risk associated with that factor. In some embodiments, the risk weight may vary based on the value of the associated field. For example, risk weight may change with age ranges, blood pressure ranges, etc. The risk weight may be used (e.g. by another entity such as HCP 120 and/or PMDP 130 and/or a pharmacy and/or another entity administering the drug/device) to compute a score for each candidate patient. Based on individual scores and/or known collective demographic information for communities (e.g. provided by PHE 180 via sub-block 680-1), an entity such as PMDP 130 may determine a collective score for a community, and determine priority in terms of where batches of produced drugs are to be shipped. The score may also be used (e.g. by HCP 120, or an entity administering the drug/device at a location) to determine priority and schedule patients to receive a drug/device that is being deployed. In some embodiments, demographic criteria 610 may form part of a PHER sub-block 680-1.

Deployment criteria 604 may also include deployment information 620 such as disease 622 associated with a current outbreak, diagnostic 624 (e.g. used to determine if a patient tests positive for disease 622), drugs/devices 626 (e.g. vaccines, drugs, protective health equipment, ventilators, etc.) used for prevention and/or treatment, and procedures 628 to be followed during administration of drugs/devices 626. Drugs/devices field 626 may include dose to be administered 636, duration of administration 636, etc. In some embodiments, deployment information 620 may form part of a PHER sub-block 680-2.

In some embodiments, PHER 600 may further include transaction ID to 695 to identify a current transaction, PMDP profile 395 with information pertaining to PMDP 130, HCP profile 295 with information pertaining to HCP 120, etc. PHER may also include other entity profiles, such as pharmacies, test administration entities, reporting entities, etc. PHER 600 may also include PHE profile 645 with information about PHE 180 such as PHE Name 642, PHE contact information 644, PHE details 648, etc., which may be used to identify and communicate with PHE 180. In some embodiments, PHE profile 645 may form part of PHER sub-block 680-3.

In some embodiments, information in sub-blocks 680-1, and/or 680-2, and/or 680-3 may be combined in a single sub-block 680 or combined in other ways. In other instances, sub-blocks 680-1, and/or 680-2, and/or 680-3 may be used at various points during a transaction to communicate information with another entity. Information in sub-blocks 680-1, and/or 680-2, and/or 680-3 may be encrypted and may be decryptable by a designated entity.

Figure 7A:
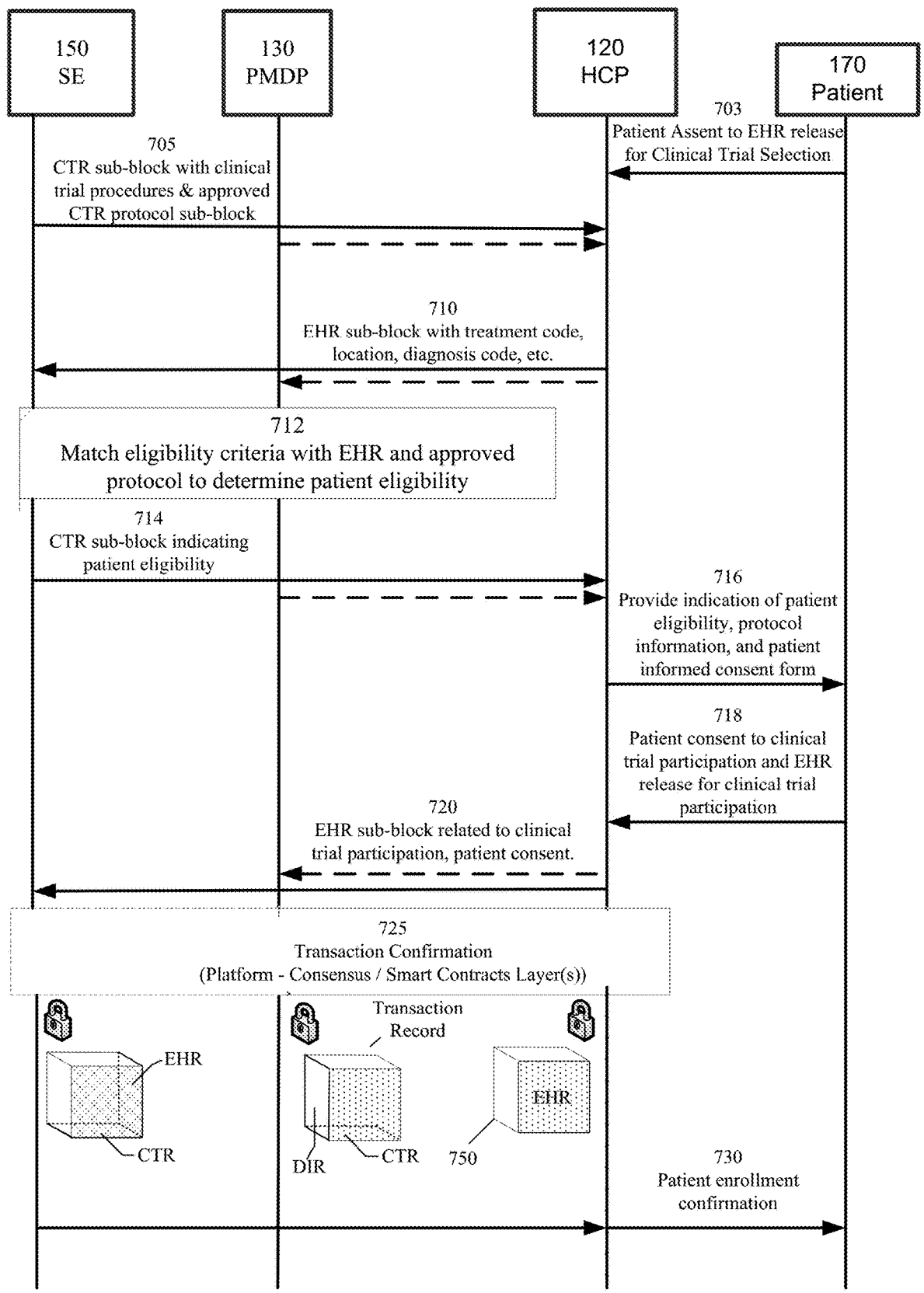
FIG. 7A shows a flow diagram illustrating an example process flow to facilitate secure clinical trial candidate selection and promote interoperability between a plurality of entities.

FIG. 7A shows a flow diagram illustrating process flow 700 to facilitate clinical trial patient selection and enrollment while promoting healthcare information security and increasing interoperability between a plurality of entities. In some embodiments, portions of process flow 700 may occur on a permissioned blockchain platform, which may be made available to subscribing and/or authorized entities. In some embodiments, some or all of flow 700 may be implemented using applications running on computing devices associated with the entities. As outlined previously, in some situations, SE 150 may be a division of or otherwise affiliated with PMDP 130 (as indicated by dashed lines in FIG. 7A).

In flow diagram 700, some routine messages have not been shown for ease of description. Further, prior to the commencement of process flow 700, SE 150 may have obtained clinical trial protocol approval and satisfied other regulatory requirements related to the trial. Information exchanges related to protocol approval are not shown in FIG. 7A. Protocol approval may involve several message exchanges between SE 150/PMDP 130 and a regulatory agency prior to protocol approval. Approved protocol for clinical trials of drug/device 255 may be stored in CTR 400 and may include eligibility criteria 410 (which may be part of sub-block 480-1) and treatment 420 (which may be part of sub-block 480-2). The approved protocol may also be stored in DIR 300 as part of sub-block 380-1. The exchange of messages between PMDP 130/SE 150 and a regulatory agency to determine and approve a protocol for a drug/device in clinical trials may occur independently of patient assent in 703.

At 703, patient 170 may indicate approval for participation in clinical drug/device trials. In some embodiments, the approval may be conveyed to HCP 120 and/or another entity. In some embodiments, HCPs 120 may obtain patient pre-approval for participation in clinical drug/device trials at any point in time (in accordance with any laws, regulations, privacy considerations, etc.) prior to release of any patient information from EHR 200. In some embodiments, at 703, the patient's assent may indicate that some limited (e.g. non-PII) information associated with patient's EHR 200 may be released (e.g. by HCP 120 to PMDP 130) for prescreening purposes. Thus, even in situations where the patient has consented to release of PII information, HCP 120 may elect to redact patient PII information that may be exchanged with SE 150 during prescreening.

As one example, patient 170 may use an application running on a mobile computing device (e.g. smartphone, tablet, laptop, etc.) to initiate a transaction. In some embodiments, the application may be provided and/or authorized by an entity associated with the permissioned blockchain platform. For example, the application (e.g. running on a mobile computing device associated with patient 170) may have been provided by a first entity (e.g. HCP 120, PMDP 130, and/or a patient access program (not shown in FIG. 7)), and use an Application Programming Interface (API) and/or other network and communication protocols to communicate with the first entity.

At 705, SE 150 (and/or PMDP 130) may initiate transmission of CTR sub-block 480 with information to initiate clinical trials of a drug/device 255. CTR sub-block 480 may include proposed protocol (e.g. treatment 337, dosage, duration, etc.), known safety information 330, etc. In some embodiments, CTR sub-block 480 may include some or all of the drug/device information in DIR sub-block 380-1. CTR sub-block 480 may be encrypted and may be decryptable by HCP 120. In some embodiments, HCP 120 may obtain drug/device information in DIR sub-block 380-1 directly from PMDP 130.

At 710, SE 150 (and/or PMDP 130) may receive EHR sub-block 280 with diagnosis code 240, treatment code 245, indications 242, and other patient information such as location, etc. In some embodiments, sub-block 280 received by SE 150 (and/or PMDP 130) at 710 may not include PII information associated with patient 170. EHR sub-block 280 may be encrypted by HCP 120 and may be decryptable by one or more designated entities (e.g. PMDP 130 or SE 150). In some embodiments, EHR sub-block 280 may comprise information for a plurality of candidate patients who have indicated their assent to prescreening for participation in a clinical trial.

In step 712, SE 150 (and/or PMDP 130) may compare eligibility criteria 410 (e.g. received by PMDP as part of sub-block 480-1) with information in EHR sub-block 280-1 (received at 710) during a prescreening step to determine eligibility of patient(s) 170 to participate in the clinical trial for drug/device 255. For example, the age (e.g. as determined from DOB 220) of patient(s) 170 may be compared with age range 412 (in sub-block 480-1) to determine if patient(s) 170 fall within an acceptable age range. Other parameters including demographic information associated with the health record(s) of patient(s) 170 (e.g. as provided in EHR sub-block 280) may also be compared with corresponding parameters in eligibility criteria 410 ((received as part of sub-block 480-1) to determine patient eligibility. In step 712, a subset of patients eligible to participate in the clinical trial for drug/device 255 may be determined.

At 714, PMDP 130, based on the eligibility determination in step 712, an indication of the subset of candidate patients determined to be eligible may be sent by PMDP 130 (and/or SE 150) to HCP 120 along with CTR sub-block 480 (which may include relevant portions of DIR sub-block 380). The subset of candidate patients determined to eligible may be no greater than the number of candidate patients (at 710) because some patients may be determined to be ineligible in step 712.

At 716, HCP 120 may provide an indication of patient eligibility to eligible patient(s) 170 based on the indication of patient eligibility (received at 714) along with protocol information and an informed consent form for patient consent/approval.

In some embodiments, HCP 120 may provide coverage related information 272, drug/device information 255, and clinical trial related information and Plan ID 270 to Payer 140 in encrypted sub-blocks 282 (not shown in FIG. 7A), which may be decryptable by the respective receiving entity. Payer 140 may respond with additional encrypted sub-blocks (not shown in FIG. 7A) decryptable by HCP 120 validating patient coverage, indicating whether the clinical trial would be covered under the patient's plan, and indicating patient cost. In some embodiments, coverage related information (including costs) may be sent to patient 170 at 716 (or prior to obtaining patient consent at 718).

At 718, one or more eligible patients 170 may indicate consent to participate in the clinical trial for drug/device 255 (e.g. after reviewing the information received at 716 and/or consulting with HCP 120) and may also consent to sharing of information associated with respective EHRs 200 with SE 150 (and/or PMDP 130). In some embodiments, patients 170 may also indicate their consent electronically (e.g. via an application on a mobile phone or computing device) subject to any legal, regulatory, or trial specific requirements.

At 720, SE 150 (and/or PMDP 130) may receive from HCP 120, a list of eligible prescreened patients who have consented to participation in the clinical trial for drug/device 255 along with EHR information for the patients 170, which may include PII information for patients 170. The list of patients at 720 may differ from the subset of eligible patients at 714 because some patients may not consent to participation.

In some embodiments, steps 710, 712, 716, 718, and 720 may be repeated for a plurality of HCPs and patients 170 until SE 150 (and/or PMDP 130) indicates that the number of patients for the current clinical trial associated with drug/device 255 is adequate and/or that enrollment for the current clinical trial is closed. In some embodiments, the closure may be HCP-specific or location specific because the clinical trial protocol may diversify participants by geography (location) and by HCP. Thus, the enrollment may remain open for other HCPs or patients/HCPs in other locations.

At 725, upon approval by PMDP 130 and/or SE 150 and/or Payer 140 (e.g. when payments to participants are to be made and/or an insurer agrees to compensate SE 150 and/or PMDP 130 for compassionate/experimental use of a drug/device on a patient 170), the platform (e.g. private permissioned blockchain platform) may send transaction ID 695 and a transaction type indicating transaction confirmation to entities associated with the transaction. Upon receiving the confirmation each entity may add its respective encrypted record (e.g. EHR 200 for HCP 120, DIR record 300 for PMDP 120, CTR 400 for SE 150, and HTR for Payer 140) to a local blockchain. In addition, two or more of the above encrypted records may form part of a multi-dimensional block 750 in a multi-dimensional blockchain (not shown in FIG. 7A). An encrypted block (e.g. EHR 200 for HCP 120, DIR 300 for PMDP 130, CTR 400 for SE 150, and HTR 500 for SE 150 and/or Payer 140) in the multi-dimensional block may be decrypted by the entity encrypting the block and may not be decrypted by any other entity. Thus, while each block represents an entity's view of the transaction, the view is consistent with the views of other entities in relation to the same transaction because each block includes (via received sub-blocks) approved information from other related entities at the time of transaction finalization. In addition, while each multi-dimensional block in the multi-dimensional blockchain represents a snapshot of a finalized transaction as seen by entities that are party to the transaction, information in any single encrypted block (e.g. one of EHR 200, DIR 300, CTR 400, or HTR 500 in FIG. 7A) that is owned and encrypted by a specific entity (e.g. one of HCP 120, PMDP 120, SE 150, or SE 150/Payer 140, respectively, in FIG. 7A) is shielded from non-owning entities. As shown in FIG. 7A, multi-dimensional block 750 is visualized as a cube (a multi-dimensional volume) with each face of the cube representing a block associated with an entity that is party to the transaction. In the event that the transaction is not approved by SE 150 and/or another entity, one or more of steps 710 through 725 may be repeated.

At 730, SE 150 (and/or PMDP 130) and/or HCP 120 or the platform may send an enrollment confirmation to enrolled patients 170. The set of enrolled patients at 730 may differ from the set of eligible patients who have indicated approval to participate in the clinical trial (at 720) because PMDP 130 (and/or SE 150) may not enroll some patients based on further screening and/or because of protocol or other considerations.

Figure 7B:
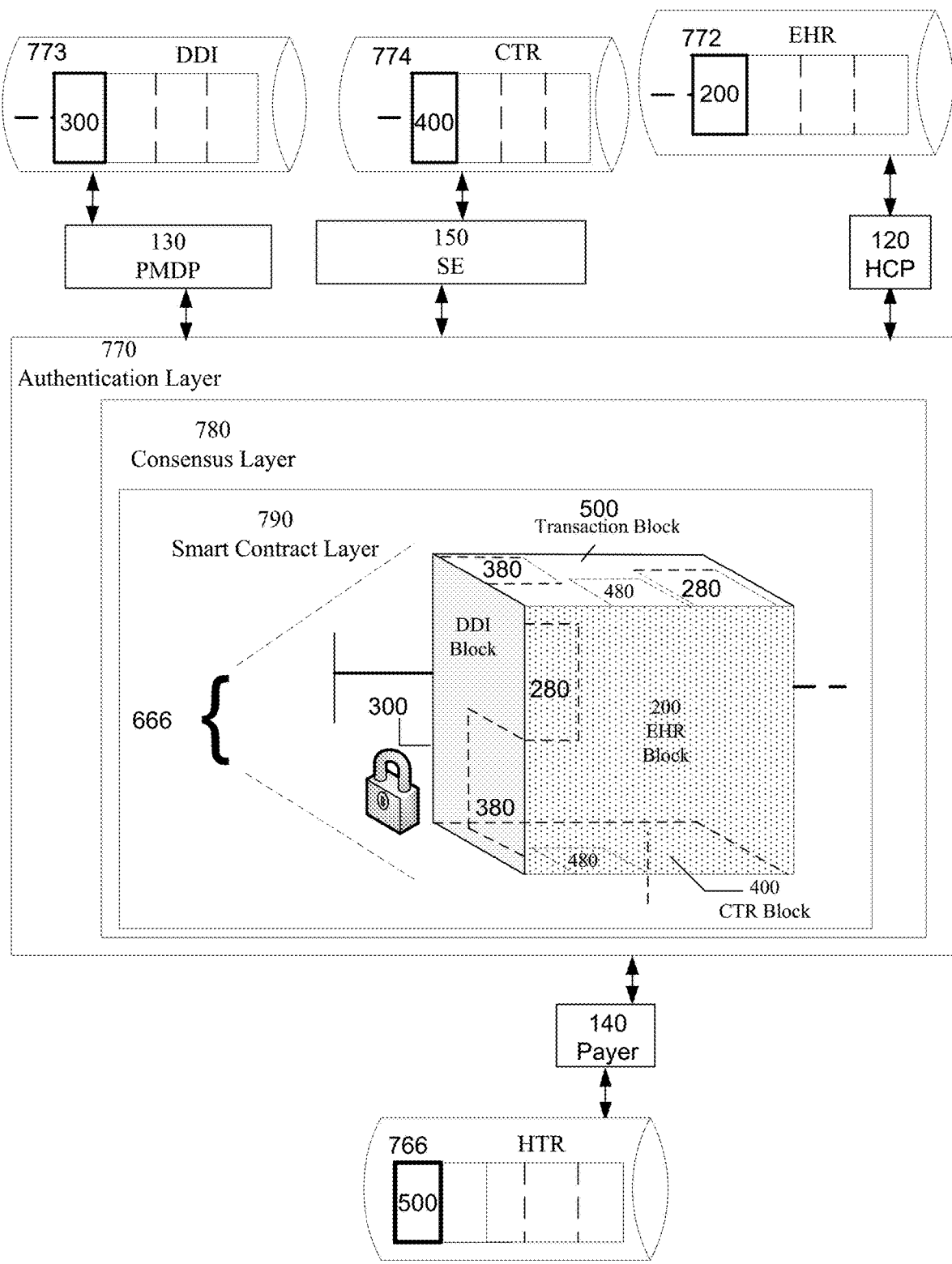
FIG. 7B shows entities and layers associated with an example platform to facilitate secure clinical trial candidate selection and promote healthcare system interoperability.

FIG. 7B depicts entities and layers associated with an example platform to facilitate healthcare system security and interoperability. In some embodiments, the various entities HCP 120, PMDP 130, SE 150, Payer 140 etc. may form part of a permissioned blockchain platform. In a permissioned blockchain platform, trusted entities may form a platform and invite other trusted entities to join the network. In some embodiments, the permissioned blockchain platform may also be private (e.g. to invited and/or authorized entities). In some embodiments, the permissioned blockchain platform may support multi-dimensional blockchains. Rules pertaining to access and adding blocks to the multi-dimensional blockchain, program code to determine contracts between the entities (e.g. smart contracts), applications that leverage platform functionality (e.g. on behalf of a patient 170), validation of updates, etc. may be determined and/or authorized by entities associated with the permissioned blockchain platform. As outlined previously, in some situations, PMDP 130 and Payer 140 may be divisions of and/or otherwise affiliated with SE 150.

In some embodiments, the permissioned blockchain platform may take the form of a cloud-based system. A cloud-based system refers to infrastructure, applications, services, and/or other resources (including hardware resources) that may be made available over a network (e.g. the Internet). Cloud-based systems may be based on underlying hardware and software resources and may be public (e.g. available on a fee basis to all), private (e.g. limited to an organization), or a hybrid (using some combination of public and private clouds). In some embodiments, the entities associated with the platform may be represented by servers (hardware and/or software), which, in some instances, may be cloud based. For example, HCP 120, PMDP 130, Payer 140 and various other entities (such as the FDA, IRB, CTRB, DSMB, etc. (not shown in FIG. 7B) may be associated with the private permissioned blockchain platform and) may include agents running on servers, and/or agents running on cloud-based platforms including Virtual Machines (VMs).

In some embodiments, access to functionality afforded by the permissioned blockchain platform may be facilitated through a layer or an API associated with the platform. For example, patients 170 and/or another authorized entity acting on behalf of a patient (e.g. an entity facilitating access to payment assistance programs offered by PMDPs 130) may provide a mobile application (e.g. running on a smartphone or other mobile computing device) that interacts with the cloud based permissioned blockchain platform to facilitate: (a) determination of patient choices and associated cost metrics associated with an initial prescription (e.g. as indicated by data in sub-block 280-1 in FIG. 7A) for a patient 170 based on patient criteria 297 and (b prescription finalization (e.g. as indicated by data in sub-block 280-2 in FIG. 7A) in conjunction with the delivery of payment assistance to patient 170.

As shown in FIG. 7B, multi-dimensional block 750 includes EHR information block 200, DIR information block 300, CTR information block 400, and HTR information block 500. In some embodiments, multi-dimensional block 750 may form part of a multi-dimensional blockchain.

In multi-dimensional block 750, EHR information block 200, DIR information block 300, CTR information block 400, and HTR information block 500 may be encrypted and decryptable by HCP 120, PMDP 130, SE 150, and Payer 140, respectively.

Further, EHR information block 200, DIR information block 300, CTR information block 400, and HTR information block 600 may also form blocks in EHR blockchain 772, DIR blockchain 773, CTR blockchain 774, and HTR blockchain 766, respectively. As shown in FIG. 7B, EHR blockchain 772, DIR blockchain 773, CTR blockchain 774, and HTR blockchain 766 may be owned and locally maintained by HCP 120, PMDP 130, SE 150, and Payer 140, respectively. FIG. 7B also depicts sub-block 280 (which forms part of EHR block 200), sub-blocks 380 (which forms part of DIR block 300) and sub-block 480 (which forms part of CTR block 400). As outlined above, information in the sub-blocks may have been shared between some of the entities associated with a transaction prior to transaction finalization and (at the time of transaction finalization) may be consistent across a plurality of blocks that form part of multi-dimensional block 750. In some embodiments, each field associated with information blocks 200, 300, 400, 500 and/or 600 may have a unique global field id, which may uniquely identify the field within the multi-dimensional blockchain system and/or to relevant entities, when information pertaining to that field is shared between entities. Multi-dimensional blocks may include data and a timestamp. Timestamps may determine the order in which multi-dimensional blocks (once finalized) are linked.

As shown in FIG. 7B, HCP 120, PMDP 130, SE 150, and Payer 140 may interact with authentication layer 770. Authentication layer 770, may include functionality for identification and management (adding, registering, authorizing, and deleting) of system entities and/or applications (e.g. mobile applications) that use (or request use to) functionality provided by the permissioned blockchain platform. In addition, authentication layer may include functionality to validate permissions related to operations involving: (a) the multi-dimensional blockchain (adding new blocks, creating links, etc.); (b) transaction types (e.g. whether an entity may initiate or participate in a specified transaction type), etc. Authentication layer 770 may interact with consensus layer 780, which may include functionality to determine the ordering of transactions and validate correctness of a set of transactions related to multi-dimensional block 750.

In some embodiments, consensus layer 780 may confirm the correctness of transactions that constitute the multi-dimensional block. At the time of transaction finalization, a consensus technique applied by consensus layer 780 may confirm the correctness of transactions (including shared data between entities) that constitute the multi-dimensional block. In some embodiments, consensus techniques such as Byzantine Fault Tolerance (BFT) or variations thereof such as Redundant BFT, Fast Byzantine Consensus, Dynamic Quorums, or some other voting-based consensus technique may be used to determine if a multi-dimensional block 750 may be formed using component blocks (e.g. EHR information block 200, DIR information block 300, CTR information block 400, and HTR information block 500). When an authorized entity (e.g. Payer 140 or a designated authoritative entity for a transaction/transaction type) or some specified number (e.g. all or a majority) of entities validates a transaction or block, then consensus is achieved. Determination of consensus or transaction validation may vary depending on the transaction type.

If the transaction is confirmed as correct by the consensus technique, then a first instance of an unlocked multi-dimensional block 750 may be formed. As shown in FIG. 7B, unlocked multi-dimensional block 750 may be locked and added to the multi-dimensional block when the transaction is finalized. In some embodiments, blocks that form part of multi-dimensional block 750 (e.g. EHR information block 200, DIR information block 300, PBR information block 400, PPR information block 500, and HTR information block 600) may also be added as blocks to respective local blockchains (e.g. EHR blockchain 772, DIR blockchain 773, PBR blockchain 764, PPR blockchain 775, and HTR blockchain 766, respectively) at the time of transaction finalization and upon locking of multi-dimensional block 750. Thus, information in the locally stored block (e.g. EHR information block 200, DIR information block 300, PBR information block 400, PPR information block 500, and HTR information block 600) is also consistent with information in multi-dimensional block 750.

On the other hand, if, for example, a patient identified in Patient ID 425 in sub-block 480 does not match a Patient ID (e.g. in sub-block 280), the transaction may be deemed incorrect and the block addition request may be rejected. In some embodiments, the platform, or each entity may maintain a log of rejected transactions for traceability and debugging purposes. The log may indicate reasons or codes associated with transaction rejection.

In some embodiments, consensus layer 780 may apply consensus techniques and may interact with a smart contracts layer 790 to establish transaction correctness and/or validity and initiate further actions. Smart Contracts layer 790 may comprise program code that implements logic related to a blockchain. For example, "smart contract" program code associated with the multi-dimensional blockchain may process transaction requests and determine the validity of transactions based on program logic. The logic may depend on rules agreed to by the entities for transactions related to the blockchain. For example, Smart Contracts layer 790 may reject a transaction (e.g. from HCP 120) because of incompatibility between two or more drugs prescribed to a patient. Smart contracts may operate at validation time and at commit time before a block is locked and/or committed. In some embodiments, smart contracts layer 790 may encode rules or agreement between two or more entities in relation to data sharing, transactions, etc., which may be based on a real-world contract between the entities. In some embodiments, each update on a traditional blockchain (e.g. one of EHR blockchain 772, DIR blockchain 773, PBR blockchain 774, or HTR blockchain 766) may be validated by smart contract program code associated with the platform. The smart contract program code may reflect agreements between the entities in relation to data sharing, authentication, payments, etc. The smart contract layer may be viewed as an automation tool that facilitates interaction between entities without manual intervention. In some embodiments, the smart contract layer may initiate actions based on rules associated with one or more contracts when those rules have been satisfied. Each update to the multi-dimensional blockchain, and/or the passage of time, and/or other events and/or specific requests related to a contract (e.g. identified by a contract ID) may trigger actions by the smart contract layer.

The linking of updated records may be performed based on pre-defined rules agreed upon by the entities (e.g. HCP 120 and Payer 140). In some embodiments, the linking of blocks may be performed based on smart contract(s) associated with the multi-dimensional blockchain. After linking the updated blocks may be rehashed. As outlined above, the links may allow an entity to correlate information in its blockchain with information in a blockchain maintained by another entity. In addition, the entities may be able to determine a transaction or transactions associated with information in a specific block maintained by that entity. Accordingly, two or more entities may have a coherent and consistent view of transactions associated with blocks in distinct blockchains. During the process of formation multi-dimensional block 750 may be (at least initially) not fully formed (or a multi-dimensional block in progress)—so that blocks received from other entities may transform the current in progress (not fully formed) multi-dimensional block by adding another dimension. For example, finalized HTR 200 (with a prescription from HCP 120) may be added to current in progress multi-dimensional block as a dimension. Another dimension may then be added to the in progress multi-dimensional block—for example, a dimension with DIR 300 (with the drug/device information). The process may continue until the multi-dimensional block is fully formed (e.g. includes dimensions from all relevant parties to a transaction).

Multi-dimensional block (and its component records) may be locked upon transaction finalization to prevent further modifications and ensure a consistent view. Any subsequent modifications may result in a new multi-dimensional block being added to the multi-dimensional blockchain. For example, a new multi-dimensional block may be formed with updates to a data record for a single dimension while substantive information associated with the other dimensions may remain unchanged. For example, drug related information (e.g. new contraindications) associated with a drug prescribed to a patient may be updated (e.g. by PMDP 130) in a new multi-dimensional block without updates to other records.

The multi-dimensional block may take the form of a Merkle tree associated with a multi-dimensional block chain that includes component data records (e.g. EHR 200, DIR record 300, CTR 400, and HTR 500). As outlined earlier, the data records may also be associated with distinct individual blockchains.

Accordingly, cryptographic hashes of individual records (e.g. separate cryptographic hashes (or "hash") of EHR 200, DIR record 300, PBR 400, PPR 500 and HTR 500,) in the distinct individual blockchains (772, 773, 774, and 766, respectively) may be obtained using distinct cryptographic hash functions so that records owned by an entity are not decryptable or visible to other entities. Separate cryptographic functions (e.g. which may be known to entities associated with the permissioned blockchain platform) may be used to obtain cryptographic hashes of combinations of records so that a top hash is associated with the multi-dimensional block as a whole. In some embodiments, each multi-dimensional block may include a block header with a timestamp, top hash, information related to the previous block, a pointer to the root of Merkle tree, and other appropriate information. The hash references may take the form of uniform resource locator (URL) on the private permissioned blockchain platform and/or local (entity specific) addresses.

FIG. 7B shows a committed and locked multi-dimensional block 750, where information from sub-blocks 480, 280, and 380 has been shared between corresponding authorized relevant entities. In addition, multi-dimensional block 750 includes linkages between individual component blocks. Multi-dimensional block 750 may represent a holistic view of transaction at a point in time, in part, because it may include real world physical states associated with a drug (dosage, effects, etc.), a patient (medical condition, treatment, effect, etc.), and cost at that point in time. Multi-dimensional block 750 may also include links to a previous block in the blockchain. Validated and finalized multi-dimensional block 750 may include finalized data records 200, 300, 400, and 500, which may correspond to finalized information blocks 200, 300, 400, and 500, respectively, in corresponding distinct local blockchains 772, 773, 774, and 766, respectively.

Figure 7C:
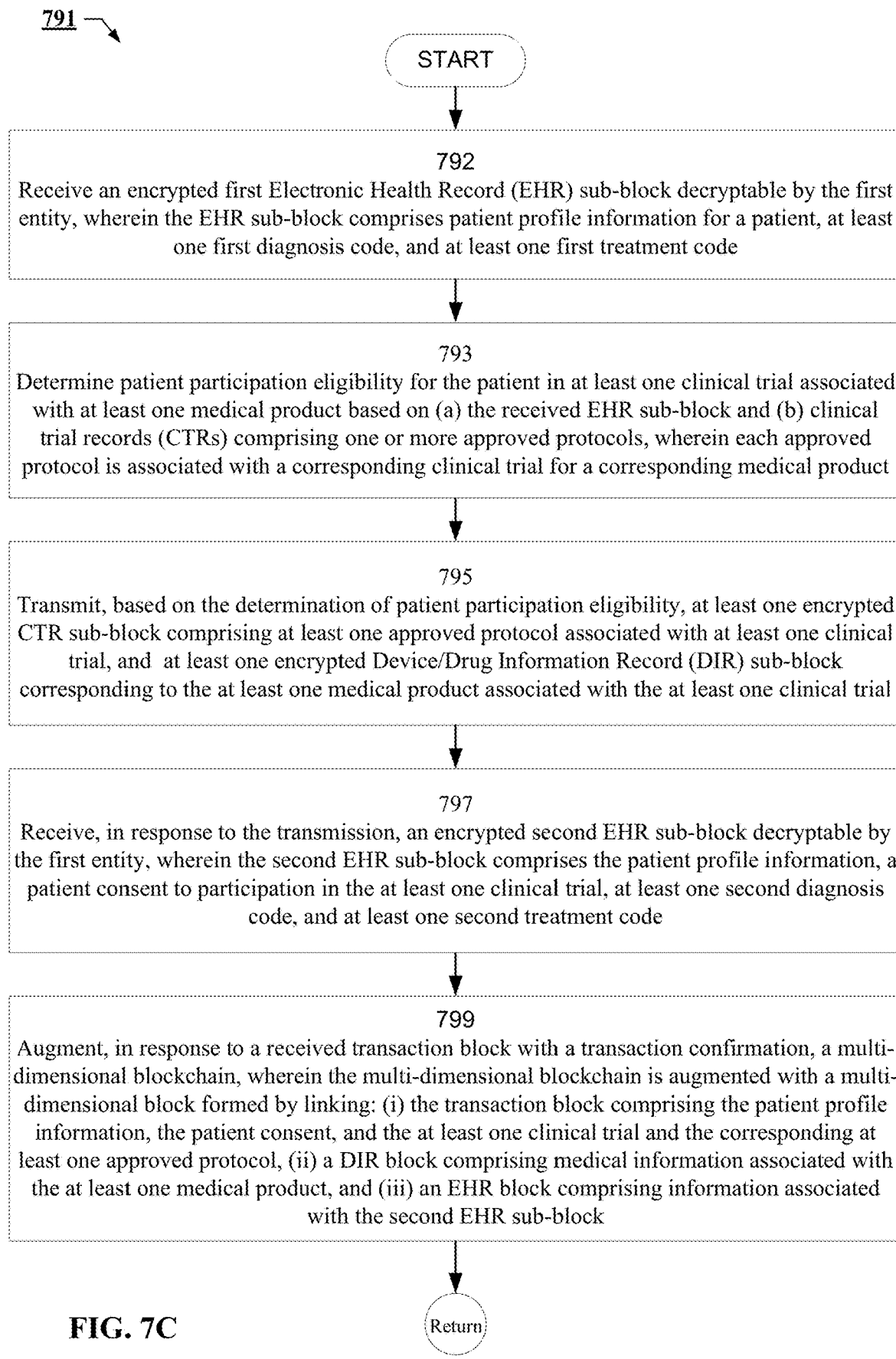
FIG. 7C shows a flowchart illustrating an example method to facilitate secure clinical trial candidate selection and promote interoperability between a plurality of entities.

FIG. 7C shows a flowchart of an exemplary method 791 to facilitate healthcare information security and interoperability while facilitating patient selection for clinical trials. In some embodiments, method 791 may use multi-dimensional blockchains, which may be based on distinct blockchains maintained by the individual entities in a system. In some embodiments, method 800 may be performed (at least in part) on a private permissioned blockchain platform, which, in some instances, may take the form of a cloud-based system. Method 791 may also be performed by a processor, computer or networks of computers such as distributed computing systems, servers (hardware and software), including application servers, mobile computing devices (e.g. smartphones, smart wearable devices, handheld computers, tablets, laptops, etc.), as well as cloud-based systems.

In some embodiments, method 791 may be performed at a first entity (e.g. PMDP 130, SE 150, etc.). For example, the first entity may comprise at least one server or a computer system associated with at least one of a pharmaceutical provider or a medical device provider such as SE 150 (and/or PMDP 130). In some embodiments, the first entity may interact with one or more second entities. The second entities may include one or more servers or computer systems associated with healthcare providers such as HCP 120, or payment/insurance providers such as Payer 140, or patients 170, etc. In some embodiments, the first entity and the one or more second entities may form computing nodes in a distributed computing system and the multi-dimensional blockchain may form part of a permissioned private blockchain platform such as permissioned private blockchain platform.

In some embodiments, method 791 may be invoked when an entity such as the first entity initiates a transaction (e.g. with a transaction ID and/or transaction type) to add a block to locally maintained blockchain. The addition of the block to the local blockchain may involve inputs from one or more other entities and the permissioned private blockchain platform may invoke method 791. In some embodiments, method 791 may be initiated in response to an approval of at least one protocol associated with at least one clinical trial for at least one medical product. The medical products may comprise: one or more drugs; and/or one or more biologics; and/or one or more medical devices; and/or a combination thereof.

In some embodiments, in step 792, a first entity (e.g. PMDP 130 or SE 150) may receive an encrypted first Electronic Health Record (EHR) sub-block (e.g. sub-block 280) decryptable by the first entity, wherein the EHR sub-block comprises patient profile information for a patient (e.g. basic profile information 230), at least one first diagnosis code (e.g. diagnosis code 240), and at least one first treatment code (e.g. treatment code 245). In some embodiments, the patient profile information in the first EHR sub-block may comprise non-personally identifiable (PII) information. When release of patent PII information is pre-authorized by the patient, the patient profile information may comprise patient personal identification information (PII). Further, in some embodiments, the patient profile information may comprise patient location information and health care provider information In some embodiments, the first entity may receive the first EHR sub-block (e.g. in step 792) upon receiving an approval of the at least one protocol associated with the at least one clinical trial. For example, the first entity may request one or more EHR sub-blocks from at least one second entity and the encrypted first EHR sub-block may be received from the at least one second entity in response to the request.

In step 793, the first entity may determine patient participation eligibility for the patient in at least one clinical trial associated with at least one medical product based on (a) the received EHR sub-block (e.g. sub-block 280) and (b) clinical trial sub-blocks (e.g. sub-blocks 480 in CTR 400 or DIR 300) comprising one or more approved protocols, wherein each approved protocol is associated with a corresponding clinical trial for a corresponding medical product.

For example, eligibility for patient participation in the at least one clinical trial may be based on information in the first EHR sub-block by determining that the patient satisfies corresponding eligibility criteria specified for the at least one clinical trial, wherein the corresponding eligibility criteria are comprised in the at least one approved protocol. In some embodiments, the corresponding eligibility criteria comprise inclusion criteria and exclusion criteria In step 795, the first entity may transmit, based on the determination of patient participation eligibility, at least one encrypted CTR sub-block (e.g. CTR sub-block 480) comprising at least one approved protocol associated with the at least one clinical trial (e.g. based on sub-block 480, and at least one encrypted Device/Drug Information Record (DIR) sub-block (e.g. DIR sub-block 380) corresponding to the at least one medical product associated with the at least one clinical trial.

In step 797, the first entity may receive, in response to the transmission, an encrypted second EHR sub-block decryptable by the first entity, wherein the second EHR sub-block comprises the patient profile information (e.g. basic profile information 230 including PII), a patient consent to participation in the at least one clinical trial, at least one second diagnosis code, and at least one second treatment code (e.g. based on the drug/device in the clinical trial). Thus, in some embodiments, patient PII may be included in the second EHR sub-block (e.g. upon selection of the patient for the clinical trial) but may not be included in the first EHR sub-block (during prescreening).

In step 799, the first entity may augment, in response to a received transaction block with a transaction confirmation, a multi-dimensional blockchain, wherein the multi-dimensional blockchain is augmented with a multi-dimensional block formed by linking: (i) a transaction block comprising the patient profile information, the patient consent, and the at least one clinical trial and the corresponding at least one approved protocol, (ii) a DIR block comprising medical information associated with the at least one medical product, and (iii) an EHR block comprising information associated with the second EHR sub-block. In some embodiments, the multi-dimensional block may further comprise a CTR block, wherein the CTR block comprises information pertaining to the at least one approved protocol.

In some embodiments, the first entity may then transmit a confirmation of enrollment of the patient in the at least one clinical trial to the patient (e.g. based on the patient PII information).

FIG. 8 shows a flow diagram illustrating process flow 800 to facilitate drug/device deployment, while promoting healthcare information security and increasing interoperability between a plurality of entities. In some embodiments, portions of process flow 800 may occur on a permissioned blockchain platform, which may be made available to subscribing and/or authorized entities. In some embodiments, some or all of flow 800 may be implemented using applications running on computing devices associated with the entities. In flow diagram 800 some routine messages have not been shown for ease of description.

At 805, PMDP 130 may obtain PHER sub-block (e.g. encrypted PHER sub-block 680 decryptable by PMDP 130) with deployment criteria from PHE 180. In some embodiments, information associated with PHER sub-block 680 may be publicly available and/or available to authorized entities and may be retrieved by PMDP 130. PHER sub-block 680 may include collective demographic information with risk factors associated with one or more population segments. For example, the collective demographic information may include demographic criteria 610 associated with drug/device deployment, which may include risk factors (e.g. associated with a disease outbreak) and location information (e.g. where the disease outbreak is prevalent, emerging, or accelerating).

At 807, HCP 120 may obtain patient authorizations to the use of EHR 200 associated with patient 170 in connection with drug/device deployment. In some embodiments, patient authorizations may include authorizations to use PII information, which may be used for drug/device dispensation. In other instances, non-PII information may be used initially (e.g. to determine eligibility at step 815 below), and PII information may be used once patient eligibility has been determined.

At 810, PMDP may receive one or more EHR sub-blocks (e.g. encrypted EHR sub-blocks 280 decryptable by PMDP 130) with patient profile and medical history information. EHR sub-blocks 280 sent at 810 may be based on authorizations obtained at 807. Patient authorizations may be obtained at any time prior to 810 and, in some instances, may be based on pre-authorizations obtained by HCP 120 in accordance with prevailing laws and regulations.

In step 815, PMDP 130 may compare deployment criteria (e.g. based on sub-block 680) with EHR and demographic information (e.g. based on sub-blocks 280) to determine a set of eligible patients. For example, information in the EHR sub-blocks (e.g. sub-blocks 280) may be compared with eligibility criteria for drug/device deployment (e.g. deployment criteria 604 including collective demographic information such as age groups, occupations, locations, etc. that may be at increased risk) to determine candidate patients eligible to receive the drugs/devices on a priority basis and/or currently eligible to receive the drugs/devices. The set of patients 170 eligible to receive drugs/devices may be some subset of the patients 170 associated with the EHR sub-blocks 280 sent to PMDP 130 at 810.

At 820, PMDP 130 may transmit, one or more encrypted DIR sub-blocks 380 decryptable by one or more corresponding second entities (e.g. HCP 120 and/or Pharmacy 160, which may be used by patient 170 to obtain prescribed drugs/devices), with an indication of patient eligibility to receive the drugs/devices (based on the determination at 815). wherein each transmitted first sub-block comprises at least one candidate patient profile and medical information associated with the at least one treatment. For example, PMDP 130 may transmit candidate patient profiles corresponding to the candidate patients that are eligible to receive the drug/device on a prioritized basis to HCPs 120 (and optionally, to Pharmacies 160—e.g. designated by PHE 180 and/or based on information in the patient profiles).

At 825, HCP 120 may confirm patient eligibility to receive the drugs/devices to patient 170. At 830, HCP 120 may send an EHR sub-block (e.g. encrypted sub-block 280 decryptable by Payer 140) to Payer 140 to confirm coverage information for eligible patient 170. At 835, Payer 140 may transmit HTR sub-block (e.g. encrypted HTR sub-block 580-1 confirming patient coverage) to HCP 120.

At 840, HCP 120 may transmit prescription information in an EHR sub-block blocks (e.g. encrypted EHR sub-blocks 280 decryptable by PMDP 130) to Pharmacy 160 and, optionally, to PMDP 130 and/or PHE 180 to confirm that the drug/device has been prescribed to patient 170. While information included in EHR sub-blocks 280 sent to Payer 140, PMDP 130, PHE 180 and Pharmacy 160 by HCP 120 may be consistent, the data fields that are included in the respective sub-blocks may differ and depend on the informational interface between the entities (which may depend on laws/regulations governing patient health related information as well as laws/regulations governing information exchange between the entities).

At 845, upon approval PMDP 130 and/or HCP 120, the platform (e.g. private permissioned blockchain platform) may send transaction ID 695 and a transaction type indicating transaction confirmation to entities associated with the transaction. Upon receiving the confirmation, each entity may add its respective encrypted record (e.g. EHR 200 for HCP 120, DIR record 300 for PMDP 120, HTR for Payer 140 and, PHER 600 for PHE 180) to a local blockchain. In addition, two or more of the above encrypted records may form part of a multi-dimensional block in a multi-dimensional blockchain (not shown in FIG. 8). An encrypted block (e.g. EHR 200 for HCP 120, DIR 300 for PMDP 130, PHER 600 for PHE 180, and HTR 500 for Payer 140) in the multi-dimensional block may be decrypted by the entity encrypting the block and may not be decrypted by any other entity. Thus, while each block represents an entity's view of the transaction, the view is consistent with the views of other entities in relation to the same transaction because each block includes (via received sub-blocks) approved information from other related entities at the time of transaction finalization. In addition, while each multi-dimensional block in the multi-dimensional blockchain represents a snapshot of a finalized transaction as seen by entities that are party to the transaction, information in any single encrypted block (e.g. one of EHR 200, DIR 300, CTR 400, or HTR 500 in FIG. 7A) that is owned and encrypted by a specific entity (e.g. one of HCP 120, PMDP 120, PHE 180, Pharmacy 160, or Payer 140, respectively, in FIG. 8) is shielded from non-owning entities. In the event that a transaction is not approved by an entity (e.g. HCP 120 and/or PMDP 130 and/or another entity), one or more of steps 805 through 840 may be repeated.

At 850, Pharmacy 160 may send a prescription confirmation to Patient 170. When the prescription is dispensed (e.g. delivered or shipped to patient 170), then, at 855, pharmacy 160 may send information pertaining to the dispensation of the drug/device to one or more of PMDP 130, HCP 120, and/or PHE 180. The information may be used, for example, by PHE 180 to update PHE aggregate information related to the dispensation of the drugs/devices. For example, an application (e.g. on a smartphone or other mobile computing device associated with patient 170) may receive a confirmation of enrollment in the at least one selected plan (e.g. via a secure message or via a secure API communicatively coupled to the private permissioned blockchain platform PMDP 130 (and/or HCP 120 and/or SE 150) or the platform may send an enrollment confirmation to enrolled patients 170. The set of enrolled patients at 730 may differ from the set of eligible patients who have indicated approval to participate in the clinical trial (at 720) because PMDP 130 (and/or SE 150) may not enroll some patients based on further screening and/or because of protocol or other considerations.

Figure 9:
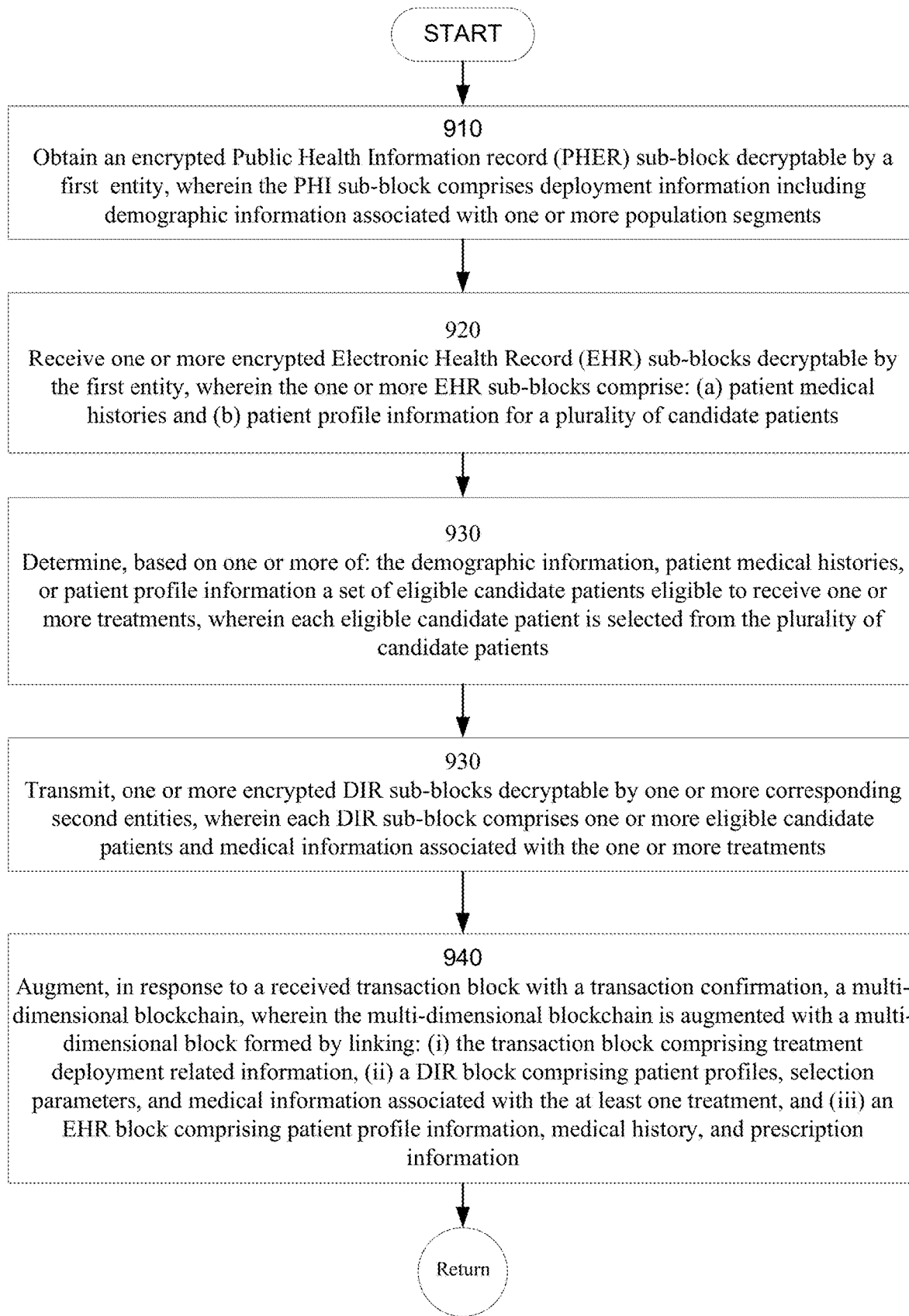
FIG. 9 shows a flowchart of an exemplary method to facilitate healthcare information security and interoperability while facilitating secure drug/device deployment and promoting interoperability between a plurality of entities.

FIG. 9 shows a flowchart of an exemplary method 900 to facilitate healthcare information security and interoperability while facilitating drug/device deployment. In some embodiments, method 900 may use multi-dimensional blockchains, which may be based on distinct blockchains maintained by the individual entities in a system. In some embodiments, method 900 may be performed (at least in part) on a private permissioned blockchain platform, which, in some instances, may take the form of a cloud-based system. Method 900 may also be performed by a processor, computer or networks of computers such as distributed computing systems, servers (hardware and software), including application servers, mobile computing devices (e.g. smartphones, smart wearable devices, handheld computers, tablets, laptops, etc.), as well as cloud-based systems.

In some embodiments, method 900 may be performed at a first entity (e.g. PMDP 130.). For example, the first entity may comprise at least one server or a computer system associated with at least one of a pharmaceutical provider or a medical device provider such as PMDP 130. In some embodiments, the first entity may interact with one or more second entities. The second entities may include one or more servers or computer systems associated with healthcare providers such as HCP 120, or insurance providers such as PHE 180, Payer 140, or patients 170, etc. In some embodiments, the first entity and the one or more second entities may form computing nodes in a distributed computing system and the multi-dimensional blockchain may form part of a permissioned private blockchain platform such as permissioned private blockchain platform.

In some embodiments, method 900 may be invoked when an entity such as the first entity initiates a transaction (e.g. with a transaction ID and/or transaction type) to add a block to locally maintained blockchain. The addition of the block to the local blockchain may involve inputs from one or more other entities and the permissioned private blockchain platform may invoke method 900. In some embodiments, method 900 may be initiated in response to the approval (e.g. after a successful clinical trial) of a medical product. The medical products may comprise: one or more drugs; and/or one or more biologics; and/or one or more medical devices; and/or a combination thereof. In some embodiments, the deployment of the medical product may occur during an emergent health situation, or in situations where availability of the medical product is limited (e.g. because full production has not commenced or production is being ramped up), to ensure that medical product is provided in accordance with public health guidelines and/or to improve overall health outcomes.

Accordingly the deployment criteria may be based on demographic criteria associated with an elevated risk from the public health emergency infection and may include: locations at risk and collective demographic information corresponding to the population segments at elevated risk. For example, the public health emergency may be a disease outbreak such as a localized disease outbreak, an epidemic, or a pandemic. In the emergency situations identified above, it may be advantageous to deploy prophylactic treatments (e.g. vaccines), other prophylactic devices (e.g. protective equipment), treatments (e.g. to lessen symptoms), therapeutic agents (e.g. curative), and/or other drugs, and/or devices in a population based on demographics and/or risk. For example, it may be advantageous deploy the treatments to first responders, medical personnel, emergency/essential personnel, and/or other population segments that may be especially vulnerable. Moreover, in some instances, (e.g. such as the Covid-19 pandemic), mass drug/device deployment may occur very soon after successful completion of a clinical trial. Therefore, techniques presented herein may facilitate more effective patient prescreening and selection, quicker ramp up of the clinical trial, and effective drug/device deployment upon completion of the trial thereby supporting efforts to address the public health emergency.

In step 910, the first entity (e.g. PMDP 130) may obtain an encrypted PHER sub-block (e.g. PHER sub-block 680) decryptable by the first entity, wherein the PHER sub-block may comprise deployment information (e.g. deployment criteria 604) including demographic information associated with one or more population segments. In some embodiments, information associated with PHER sub-block 680 may be publicly available and/or available to authorized entities and may be retrieved by PMDP 130. PHER sub-block 680 may include collective demographic information with risk factors associated with one or more population segments. For example, the collective demographic information may include demographic criteria 610 associated with drug/device deployment, which may include risk factors (e.g. associated with a disease outbreak) and location information (e.g. where the disease outbreak is prevalent, emerging, or accelerating).

In step 920, the first entity may receive one or more encrypted Electronic Health Record (EHR) sub-blocks (e.g. EHR sub-blocks 280) decryptable by the first entity, wherein each of the one or more EHR sub-blocks are associated with corresponding candidate patients, wherein the EHR sub-blocks comprise: (a) patient medical histories and (b) patient profile information for a plurality of candidate patients (e.g. basic profile information 230 with medical history 232 and, optionally diagnosis 235, when applicable). In some embodiments, EHR sub-blocks 280 received may be based on patient authorizations or pre-authorizations, which may be obtained by HCP 120 and/or requested by PMDP 130 in accordance with any prevailing laws and regulations.

In some embodiments, in step 930, the first entity may determine, based on one or more of: the demographic information, patient medical histories, or patient profile information a set of eligible candidate patients who are eligible to receive one or more treatments, wherein each eligible candidate patient is selected from the plurality of candidate patients (associated with EHR blocks received in step 920).

For example, a first entity such as PMDP 130 may compare deployment criteria (e.g. based on sub-block 680) with EHR and demographic information (e.g. based on sub-blocks 280) to determine a set of eligible patients. For example, information in the EHR sub-blocks (e.g. sub-blocks 280) may be compared with eligibility criteria for drug/device deployment (e.g. deployment criteria 604 including collective demographic information such as age groups, occupations, locations, etc. that may be at increased risk) to determine candidate patients eligible to receive the drugs/devices on a priority basis and/or currently eligible to receive the drugs/devices. The set of eligible candidate patients (determined in step 930) to receive drugs/devices may be some subset of the plurality of candidate patients (associated with the EHR sub-blocks 280 sent to PMDP 130 in step 920).

In step 930, the first entity may transmit one or more encrypted DIR sub-blocks (e.g. DIR sub-blocks 380) decryptable by one or more corresponding second entities, wherein each DIR sub-block comprises one or more eligible candidate patients and medical information associated with the one or more treatments (e.g. drugs/devices being prescribed). For example, PMDP 130 may transmit candidate patient profiles corresponding to the candidate patients that are eligible to receive the drug/device on a prioritized basis to HCPs 120 (and optionally, to Pharmacies 160—e.g. designated by PHE 180 to dispense the drugs/devices and/or based on information in the patient profiles in EHR sub-blocks 280).

In step 940, the first entity may, in response to a received transaction block with a transaction confirmation, augment a multi-dimensional blockchain with a multi-dimensional block formed by linking: (i) the transaction block comprising treatment deployment related information, (ii) a DIR block comprising patient profiles, selection parameters, and medical information associated with the at least one treatment, and (iii) an EHR block comprising patient profile information, medical history, and prescription information.

In some embodiments, in step 950, the first entity, may receive transaction block with a transaction confirmation, and, in response to the received transaction block, may augment a multi-dimensional blockchain. The multi-dimensional blockchain may be augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment. For example, in a clinical trial setting, the multi-dimensional block (to augment the multi-dimensional blockchain) may include the transaction block (e.g. HTR 500) with information pertaining to the transaction, a DIR block (e.g. DIR record 300) with the medical information associated with the at least one treatment linked to an EHR block (e.g. EHR record 200) comprising candidate patient profile information for candidate patients with confirmed participation in the clinical trial.

As outlined above, in step 930, the at least one treatment may form part of at least one clinical trial. The at least one clinical trial may be associated with a corresponding clinical trial protocol comprising the corresponding eligibility criteria. In some embodiments, the corresponding eligibility criteria may comprise: one or more corresponding exclusion criteria to determine the one or more patients ineligible for inclusion in the subset of candidate patients, and one or more corresponding inclusion criteria to determine the one or patients potentially eligible for inclusion in the subset of candidate patients. In some embodiments, method 900 may be initiated in response to an approval of the corresponding clinical trial protocol associated with the at least one clinical trial. The at least one clinical trial may be associated with: one or more drugs; or one or more biologics; or one or more medical devices; or a combination thereof.

Figure 10:
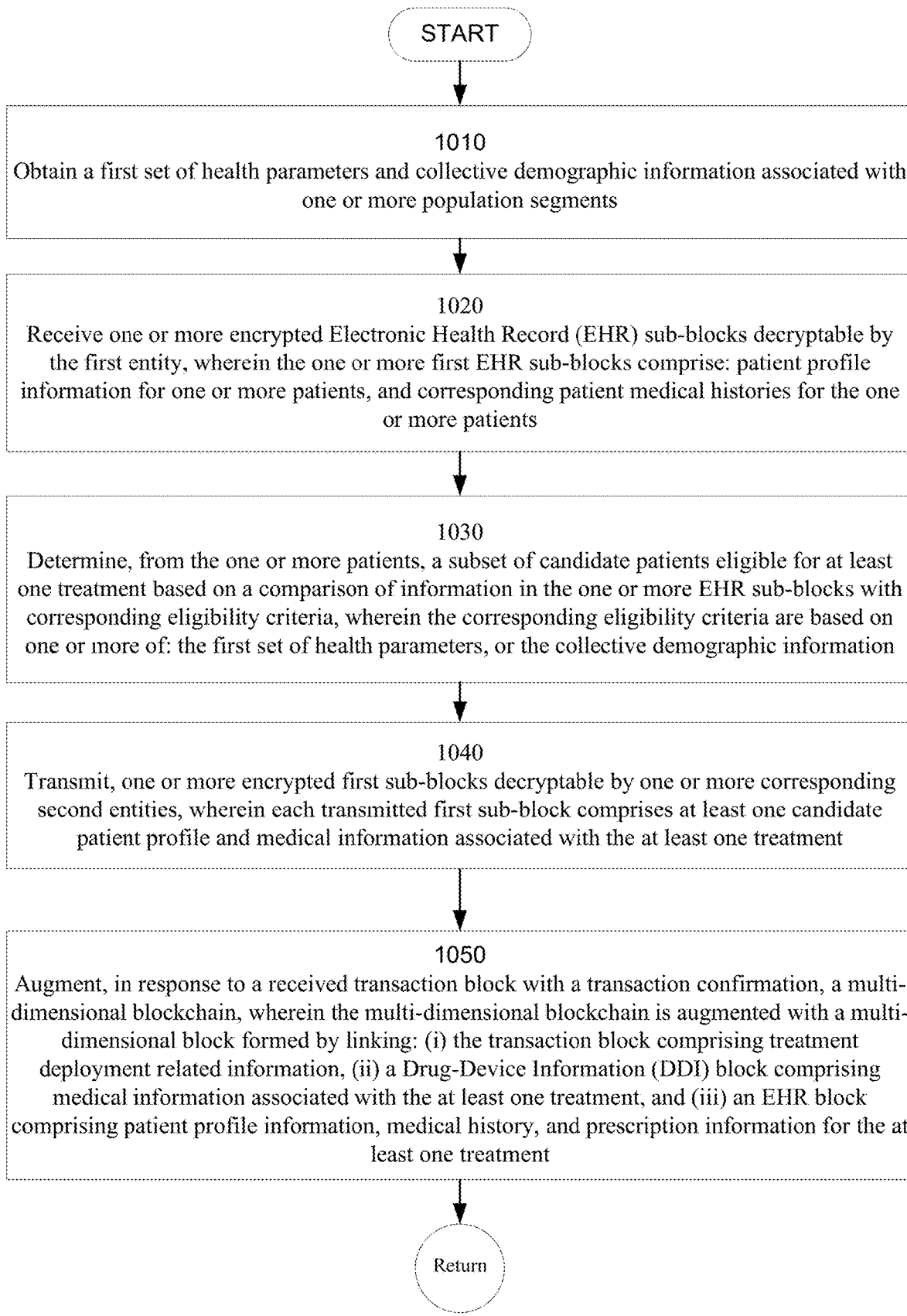
FIG. 10 shows a flowchart of an exemplary method 1000 to facilitate patient selection for clinical trial participation and/or drug/device deployment.

Further, the multi-dimensional block, in step 940, may be further augmented with a Clinical Trial Record (CTR) block (e.g. CTR 400) comprising the at least one candidate patient profile, the medical information associated with the at least one treatment, and the corresponding clinical trial protocol, wherein the clinical trial protocol further comprises the first set of health parameters, FIG. 10 shows a flowchart of an exemplary method 1000 to facilitate healthcare information security and interoperability while facilitating: (a) patient selection for clinical trial participation and/or (b) drug/device deployment. In some embodiments, method 1000 may use multi-dimensional blockchains, which may be based on distinct blockchains maintained by the individual entities in a system. In some embodiments, method 1000 may be performed (at least in part) on a private permissioned blockchain platform, which, in some instances, may take the form of a cloud-based system. Method 1000 may also be performed by a processor, computer or networks of computers such as distributed computing systems, servers (hardware and software), including application servers, mobile computing devices (e.g. smartphones, smart wearable devices, handheld computers, tablets, laptops, etc.), as well as cloud-based systems.

In some embodiments, method 1000 may be performed at a first entity. For example, the first entity may comprise at least one server or a computer system associated with at least one of a pharmaceutical provider or a medical device provider such as PMDP 130 and/or SE 150. In some embodiments, the first entity may interact with one or more second entities. The second entities may include one or more servers or computer systems associated with healthcare providers such as HCP 120, insurance providers such as Payer 140, or patients 170, or pharmacies. In some embodiments, the first entity and the one or more second entities may form computing nodes in a distributed computing system and the multi-dimensional blockchain may form part of a permissioned private blockchain platform such as permissioned private blockchain platform.

In some embodiments, method 1000 may be invoked when an entity such as the first entity initiates a transaction (e.g. with a transaction ID and/or transaction type) to add a block to locally maintained blockchain. The addition of the block to the local blockchain may involve inputs from one or more other entities and the permissioned private blockchain platform and/or a first entity may invoke method 1000.

In some embodiments, at step 1010, a first set of health parameters and/or collective demographic information associated with one or more population segments may be obtained by a first entity. In a clinical trial setting, the collective demographic information may include patient prescreening information (e.g. as in sub-block 480-1), which may be obtained from one or more HCPs 120 by SE 150. In a drug/device deployment setting, the collective demographic information may include demographic criteria 610 associated with drug/device deployment, which may include risk factors (e.g. associated with a disease outbreak) and location information (e.g. where the disease outbreak is prevalent, emerging, or accelerating). The collective demographic information in the drug/device deployment setting may be obtained by PMDP 130 from a Public Health Entity (PHE) such as PHE 180.

In step 1020, the first entity may receive one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients.

For example, SE 150 may receive one or more EHR sub-blocks 280 with corresponding patient profile and medical history information (which, in some instances, may be non-PII information). The patient profile information for each patient may comprise corresponding individual patient demographic information (e.g. age, sex, location, ethnicity, etc.) and the corresponding patient medical history may comprise one or more of: corresponding current and past patient medical conditions, or corresponding current and past patient diagnoses, or corresponding current and past patient treatments, or corresponding current and past patient medical conditions.

As another example, PMDP 130 may receive one or more EHR sub-blocks 280 with corresponding patient profile and medical history information (which may be non-PII) for drug/device deployment.

In step 1030, the first entity may determine, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information. For example, in a clinical trial setting, information in the EHR sub-blocks (e.g. sub-blocks 280) may be compared with eligibility criteria for the clinical trial (e.g. health parameters as in sub-blocks 480-1) to determine candidate patients eligible for participation in the clinical trial. As another example, in a drug/device deployment setting, information in the EHR sub-blocks (e.g. sub-blocks 280) may be compared with eligibility criteria for drug/device deployment (e.g. collective demographic information such as age groups, occupations, locations, etc. that may be at increased risk) to determine candidate patients eligible to receive the drugs/devices on a priority basis.

In step 1040, the first entity may transmit, one or more encrypted first sub-blocks decryptable by one or more corresponding second entities, wherein each transmitted first sub-block comprises at least one candidate patient profile and medical information associated with the at least one treatment. For example, in a clinical trial setting, SE 130 may transmit candidate patient profiles corresponding to the selected candidate patients to HCPs 120. As another example, in a drug/device deployment setting, PMDP 130 may transmit candidate patient profiles corresponding to the candidate patients that are eligible to receive the drug/device on a prioritized basis to HCPs 120.

In some embodiments, in step 1050, the first entity, may receive transaction block with a transaction confirmation, and, in response to the received transaction block, may augment a multi-dimensional blockchain. The multi-dimensional blockchain may be augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment. For example, in a clinical trial setting, the multi-dimensional block (to augment the multi-dimensional blockchain) may include the transaction block (e.g. HTR 500) with information pertaining to the transaction, a DIR block (e.g. DIR record 300) with the medical information associated with the at least one treatment linked to an EHR block (e.g. EHR record 200) comprising candidate patient profile information for candidate patients with confirmed participation in the clinical trial.

As outlined above, in step 1030, the at least one treatment may form part of at least one clinical trial. The at least one clinical trial may be associated with a corresponding clinical trial protocol comprising the corresponding eligibility criteria. In some embodiments, the corresponding eligibility criteria may comprise: one or more corresponding exclusion criteria to determine the one or more patients ineligible for inclusion in the subset of candidate patients, and one or more corresponding inclusion criteria to determine the one or patients potentially eligible for inclusion in the subset of candidate patients. In some embodiments, method 1000 may be initiated in response to an approval of the corresponding clinical trial protocol associated with the at least one clinical trial. The at least one clinical trial may be associated with: one or more drugs; or one or more biologics; or one or more medical devices; or a combination thereof.

Further, the multi-dimensional block, in step 1040, may be further augmented with a Clinical Trial Record (CTR) block (e.g. CTR 400) comprising the at least one candidate patient profile, the medical information associated with the at least one treatment, and the corresponding clinical trial protocol, wherein the clinical trial protocol further comprises the first set of health parameters, In some embodiments, in method 1000, the first entity may further: receive, in response to the transmission of the one or more encrypted first sub-blocks (e.g. in step 1040) and prior to the reception of the transaction block (e.g. in step 1050), at least one encrypted second EHR sub-block decryptable by the first entity, wherein the at least one second EHR sub-block comprises the at least one candidate patient profile and a corresponding patient consent by the at least one candidate patient to participation in the at least one clinical trial. For example, the second EHR sub-block may include candidate patient consent for participation in the clinical trial along with the candidate patient profile. In some embodiments, the patient profile information in first EHR block (e.g. in step 1020) may comprises non-personally identifiable (non-PII) information and the at least one candidate patient profile information in second EHR block may comprise PII information.

As outlined above, in step 1030, in some instances, the at least one treatment may be associated with at least one drug and/or device deployment. For example, the drug/device deployment may be initiated in response to a public health emergency and the eligibility criteria may be based further on risk parameters associated with the public health emergency, wherein the health parameters comprise the risk parameters. The risk parameters may include locations at risk and collective demographic information corresponding to the population segments may be indicative of populations at risk from the public health emergency. For example, the public health emergency may be a disease outbreak such as a localized disease outbreak, an epidemic, or a pandemic. In the emergency situations identified above, it may be advantageous to deploy prophylactic treatments (e.g. vaccines). other prophylactic devices (e.g. protective equipment), treatments (e.g. to lessen symptoms), therapeutic agents (e.g. curative), and/or other drugs, and/or devices in a population based on demographics and/or risk. For example, it may be advantageous deploy the treatments to first responders, medical personnel, emergency/essential personnel, and/or other population segments that may be especially vulnerable. Moreover, in some instances, (e.g. such as the Covid-19 pandemic), mass drug/device deployment may occur very soon after successful completion of a clinical trial. Therefore, techniques presented herein may facilitate more effective patient prescreening and selection, quicker ramp up of the clinical trial, and effective drug/device deployment upon completion of the trial thereby supporting efforts to address the public health emergency.

Figure 11:
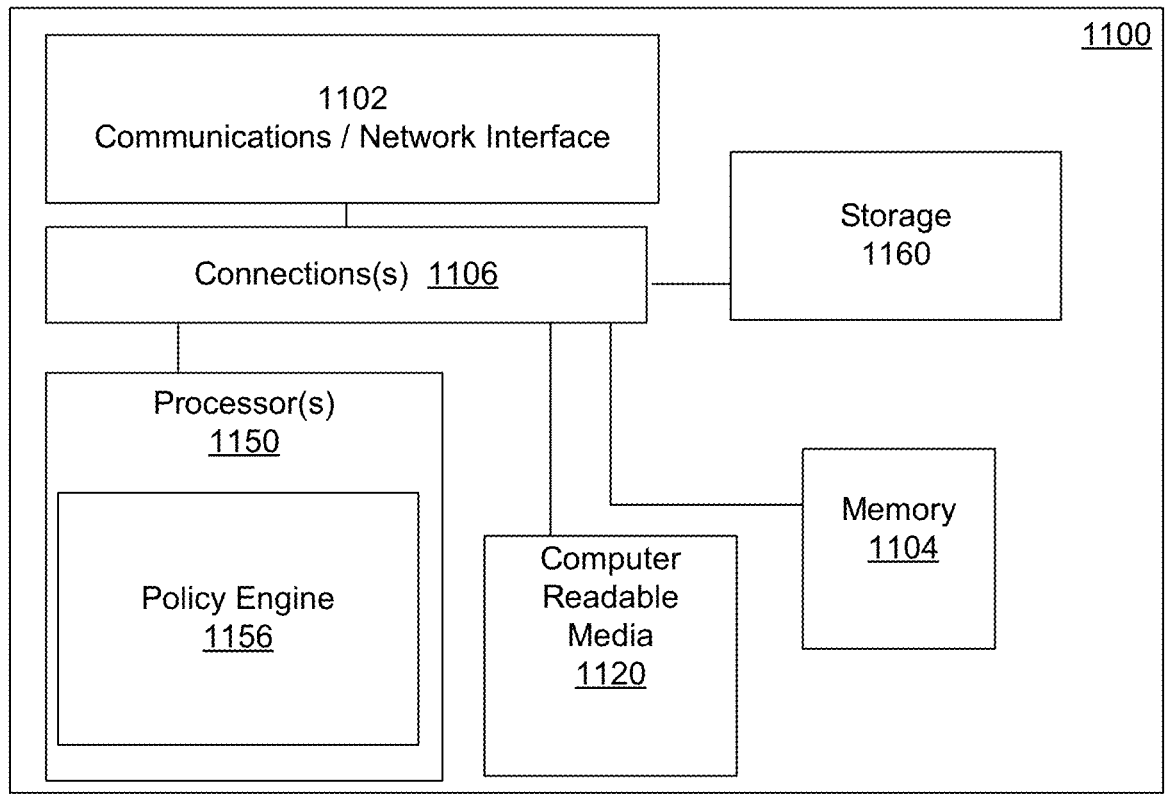
FIG. 11 shows a schematic of an exemplary computer or computing device capable of facilitating patient selection for clinical trial participation and/or drug/device deployment while supporting healthcare system security and interoperability.

FIG. 11 shows a schematic of an exemplary computer 1100 or computing device capable of facilitating healthcare system security and promoting interoperability. In some embodiments, computer 1100 may host and/or interact with a permissioned private blockchain platform. Computer 110 may be a computing device associated with an entity (e.g. HCP 120, PMDP 130, Payer 140, SE 150, Pharmacy 160, and/or PHE 180) and/or patient 170 and/or may be used to implement the permissioned blockchain platform. Computer 130 is merely an example, and several computers may be used in a networked and/or distributed fashion to implement methods and process flows disclosed herein.

In some embodiments, exemplary computer 1100 may be include (physical) servers or run servers (e.g. application servers) for one or more entities (such as HCP 120, PMDP 130, Payer 140, SE 150, Pharmacy 160, and/or PHE 180). In some embodiments, one computer 1100 may implement some or all of the process flows and/or methods and/or other techniques disclosed herein including those in FIGS. 7-10. In some embodiments, computer 1100 may form part of a distributed computing system, which may implement the permissioned private blockchain platform. In some embodiments, the distributed computing system and/or computer 1100 may be cloud-based. In some embodiments, computer 1100 may be a mobile computing device such as a smartphone, tablet, handheld, notebook, and/or laptop, which may run applications to interact with other computers 1100 and/or other applications to implement techniques disclosed herein.

In some embodiments, computer 1100/processor(s) 1150 may be able to process transaction requests, including requests related to the addition of blocks to a blockchain, including multi-dimensional blockchains. Further, computer 1100/processor(s) 1150 may be able to run encryption and/or decryption algorithms, obtain hashes of information blocks, verify hashes, perform digital signing, and may be capable of executing and/or support various methods to promote security and authentication. Authentication may refer to both the verification of the integrity of stored information (e.g. in a block in a blockchain to determine any unauthorized alterations) and ensuring that entities accessing the permissioned private blockchain platform are trustworthy and have permissions to perform any requested transactions. In some embodiments, computer 1100/processor(s) 1150 may also augment (create or add to) blockchains with new blocks (including augmenting multi-dimensional blockchains with multi-dimensional blocks).

In some embodiments, computer 1100/processor(s) 1150 may also store and execute smart contracts associated with blockchains to implement agreements related to privacy, information sharing, contractual execution, etc. between entities (e.g. HCP 120, PMDP 130, Payer 140, PHE 180, pharmacy 160, and/or patient(s) 170).

In some embodiments, computer 1100/processor(s) 1150 may be capable of mathematically analyzing and statistically compiling health related data including determining treatment classes (e.g. drug classes, device classes, and/or procedural classes) associated with a treatment, determining cost metrics, priority scores, individually, and in the aggregate, for population segments, and using patient criteria to filter and/or narrow patient selection for clinical trials. In some embodiments, computer 1100/processor(s) 1150 may also be able to initiate the display (e.g. on display 1170) of the information on a smartphone (e.g. using a Graphical User Interface (GUI). Computer 1100/processor(s) 1150 may also be capable of using machine learning techniques to determine relationships between various health parameters. For example, computer 1100/processor(s) 1150 may comprise one or more neural network processor(s), and/or distributed processors capable of being configured as a neural network, and/or be capable of executing software to model and/or simulate neural networks, which may be used to implement machine learning. For example, a PMDP 130 may use machine learning techniques based RWE information available through the multi-dimensional blocks (e.g. demographic information, side effects, drugs used in combination with a specified drug of interest, treatment outcomes etc.) to tailor usage of drug. For example, machine learning may be used to determine an effective dosage, target drugs based on demographics, improve drug interaction information, increase safety, determine the relative efficacy of various modes of administration, etc.

In some embodiments, computer 1100 may be coupled to other computers using communications/network interface 1102, which may include wired (e.g. Ethernet including Gigabit Ethernet) and wireless interfaces. Wireless interfaces may be based on: Wireless Wide Area Network (WWAN) standards such as cellular standards including 3G, 4G, and 5G standards; IEEE 802.11x standards popularly known as Wi-Fi. and/or Wireless Personal Area Networks (e.g. Bluetooth, Near Field Communication (NFC), etc.). In some embodiments, computer 110 may include Global Positioning System and/or location determination units to automatically determine location (e.g. of a patient), which may be used in conjunction with the techniques disclosed in FIGS. 7-10.

Computer 1100 may include memory 1104, which may include one or more of: Read Only Memory (ROM), Programmable Read Only Memory (PROM), Random Access Memory (RAM) of various types, Non-Volatile RAM, etc. Memory 1104 may be implemented within processor(s) 1150 or external to processor(s) 1150. As used herein, the term "memory" refers to any type of long term, short term, volatile, nonvolatile, or other memory and is not to be limited to any particular type of memory or number of memories, or type of media upon which memory is stored.

Memory may comprise cache memory, primary memory, and secondary memory. Secondary memory may include computer-readable media 1120. Computer-readable media may include magnetic and/or optical media, which, in some instances, may be removable media. Removable media may comprise optical disks such as compact-discs (CDs), laser discs, digital video discs (DVDs), blu-ray discs, and other optical media and further include USB drives, flash drives, solid state drives, memory cards etc. Computer 1100 may further include storage 1160, which may include hard drives, solid state drives (SSDs), flash memory, other non-volatile storage, and cloud-based storage.

Communications/Network interface 1102, storage 1160, memory 1104, and computer readable media 1120 may be coupled to processor(s) 1150 using connections 1106, which may take the form of a buses, lines, fibers, links, etc.

The methodologies described herein may be implemented by various means depending upon the application. For example, these methodologies may be implemented in hardware, firmware, software, or any combination thereof. For a hardware implementation, the processor(s) 1150 may be implemented within one or more application specific integrated circuits (ASICs), digital signal processors (DSPs), neural network processors (NNPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, the methodologies may be implemented with microcode, procedures, functions, and so on that perform the functions described herein. Any machine-readable medium tangibly embodying instructions may be used in implementing the methodologies described herein. For example, software may be stored in storage 1160 and/or on removable computer-readable media. Program code may be resident on computer readable media 1120, storage 1160, and/or memory 1104 and may be read and executed by processor(s) 1150.

If implemented in firmware and/or software, the functions may also be stored as one or more instructions or code computer-readable medium 1120, storage 1160, and/or memory 1104. Examples include computer-readable media encoded with data structures and computer programs. For example, computer-readable medium 1120 may include program code stored thereon may include program code to support methods to facilitate healthcare system security and promote system interoperability, including by supporting multi-dimensional blockchains, smart contracts, consensus determination and performing other function associated with a permissioned private blockchain platform as described herein.

Processor(s) 1150 may be implemented using a combination of hardware, firmware, and software. In some embodiments, computer 1100 may be coupled to a display to facilitate viewing of GUIs and interaction with administrators and other users.

Although the present disclosure is described in connection with specific embodiments for instructional purposes, the disclosure is not limited thereto. Various adaptations and modifications may be made to the disclosure without departing from the scope. Therefore, the spirit and scope of the appended claims should not be limited to the foregoing description.

What is claimed is:

1. A processor-implemented method at a first entity comprising:
    obtaining a first set of health parameters and collective demographic information associated with one or more population segments;
    receiving one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients;
    determining, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information;
    transmitting, one or more encrypted first sub-blocks decryptable by one or more corresponding second entities, wherein each transmitted first sub-block comprises at least one candidate patient profile and medical information associated with the at least one treatment; and augmenting, in response to a received transaction block with a transaction confirmation, a multi-dimensional blockchain, wherein the multi-dimensional blockchain is augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment.

2. The processor-implemented method of claim 1, wherein the at least one treatment forms part of at least one clinical trial, wherein the at least one clinical trial is associated with a corresponding clinical trial protocol comprising the corresponding eligibility criteria.

3. The processor-implemented method of claim 2, wherein the multi-dimensional block is further augmented with a Clinical Trial Record (CTR) block comprising the at least one candidate patient profile, the medical information associated with the at least one treatment, and the corresponding clinical trial protocol, wherein the clinical trial protocol further comprises the first set of health parameters.

4. The processor-implemented method of claim 2, wherein the corresponding eligibility criteria comprise: one or more corresponding exclusion criteria to determine the one or more patients ineligible for inclusion in the subset of candidate patients, and one or more corresponding inclusion criteria to determine the one or patients potentially eligible for inclusion in the subset of candidate patients.

5. The processor-implemented method of claim 2, wherein the method is initiated in response to an approval of the corresponding clinical trial protocol associated with the at least one clinical trial.

6. The processor-implemented method of claim 2, wherein the at least one clinical trial is associated with:
one or more drugs; or
one or more biologics; or
one or more medical devices; or
a combination thereof.

7. The processor-implemented method of claim 2, wherein the corresponding patient profile information for each patient comprises corresponding individual patient demographic information.

8. The processor-implemented method of claim 2, wherein, for each of the one or more patients, the corresponding patient medical history comprises one or more of: corresponding current and past patient medical conditions, or corresponding current and past patient diagnoses, or corresponding current and past patient treatments, or corresponding current and past patient medical conditions.

9. The processor implemented method of claim 2, further comprising:
receiving, in response to the transmission of the one or more encrypted first sub-blocks and prior to the reception of the transaction block, at least one encrypted second EHR sub-block decryptable by the first entity, wherein the at least one second EHR sub-block comprises the at least one candidate patient profile and a corresponding patient consent by the at least one candidate patient to participation in the at least one clinical trial.

10. The processor-implemented method of claim 9, wherein the patient profile information in first EHR block comprises non-personally identifiable (PII) information and the at least one candidate patient profile information in second EHR block comprises PII information.

11. The processor-implemented method of claim 1, wherein the at least one treatment is associated with at least one drug deployment.

12. The processor-implemented method of claim 11, wherein the at least one drug deployment is initiated in response to a public health emergency and the eligibility criteria are based further on risk parameters associated with the public health emergency, wherein the health parameters comprise the risk parameters.

13. The method of claim 12, wherein the risk parameters comprise locations at risk and the population segments indicate populations at risk from the public health emergency.

14. A computing device for a first entity comprising:
a memory,
a communications interface, and
a processor coupled to the memory and the communications interface, wherein the processor is configured to:
obtain a first set of health parameters and collective demographic information associated with one or more population segments;
receive one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients;
determine, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information;
transmit, one or more encrypted first sub-blocks decryptable by one or more corresponding second entities, wherein each transmitted first sub-block comprises at least one candidate patient profile and medical information associated with the at least one treatment; and
augment, in response to a received transaction block with a transaction confirmation, a multi-dimensional blockchain, wherein the multi-dimensional blockchain is augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment.

15. The computing device of claim 14, wherein the at least one treatment forms part of at least one clinical trial, wherein the at least one clinical trial is associated with a corresponding clinical trial protocol comprising the corresponding eligibility criteria.

16. The computing device of claim 14, wherein the at least one treatment is associated with at least one drug deployment.

17. The computing device of claim 16, wherein the at least one drug deployment is initiated in response to a public health emergency and the eligibility criteria are based further on risk parameters associated with the public health emergency, wherein the health parameters comprise the risk parameters.

18. A non-transitory computer-readable medium comprising executable instructions to configure a processor to:
- obtain a first set of health parameters and collective demographic information associated with one or more population segments;
- receive one or more encrypted first Electronic Health Record (EHR) sub-blocks decryptable by the first entity, wherein the one or more first EHR sub-blocks comprise: (a) patient profile information corresponding to one or more patients, and (b) corresponding patient medical histories for the one or more patients;
- determine, from the one or more patients, a subset of candidate patients eligible for at least one treatment based on a comparison of information in the one or more EHR sub-blocks with corresponding eligibility criteria for the at least one treatment, wherein the corresponding eligibility criteria are based on one or more of: the first set of health parameters, or the collective demographic information;
- transmit, one or more encrypted first sub-blocks decryptable by one or more corresponding second entities, wherein each transmitted first sub-block comprises at least one candidate patient profile and medical information associated with the at least one treatment; and
- augment, in response to a received transaction block with a transaction confirmation, a multi-dimensional blockchain, wherein the multi-dimensional blockchain is augmented with a multi-dimensional block formed by linking: (i) the transaction block comprising treatment deployment related information associated with the at least one treatment, (ii) A Drug-Device Information (DIR) block comprising the medical information associated with the at least one treatment, and (iii) an EHR block comprising the at least one candidate patient profile information, corresponding candidate patient medical history for the at least one candidate patient, and prescription information for the at least one treatment.

19. The non-transitory computer-readable medium of claim 18, wherein the at least one treatment forms part of at least one clinical trial, wherein the at least one clinical trial is associated with a corresponding clinical trial protocol comprising the corresponding eligibility criteria.

20. The non-transitory computer-readable medium of claim 18, wherein the at least one treatment is associated with at least one drug deployment.

* * * * *